US011103517B2

(12) United States Patent
Lowalekar et al.

(10) Patent No.: US 11,103,517 B2
(45) Date of Patent: Aug. 31, 2021

(54) PHARMACEUTICAL COMPOSITIONS FOR MINOCYCLINE

(71) Applicant: Dr. Reddy's Laboratories Ltd., Telangana (IN)

(72) Inventors: Rohit Lowalekar, Rajasthan (IN); Bijay Kumar Padhi, Odisha (IN); Rajeev Singh Raghuvanshi, Gurgaon (IN)

(73) Assignee: DR. REDDY'S LABORATORIES LTD., Telangana (IN)

( * ) Notice: Subject to any disclaimer, the term of this patent is extended or adjusted under 35 U.S.C. 154(b) by 0 days.

(21) Appl. No.: 15/093,673

(22) Filed: Apr. 7, 2016

(65) Prior Publication Data

US 2016/0296537 A1 Oct. 13, 2016

(30) Foreign Application Priority Data

Apr. 7, 2015 (IN) .......................... 1815/CHE/2015

(51) Int. Cl.
*A61K 31/65* (2006.01)
*A61K 9/20* (2006.01)
*A61K 9/00* (2006.01)
*A61K 9/28* (2006.01)

(52) U.S. Cl.
CPC ............ *A61K 31/65* (2013.01); *A61K 9/0053* (2013.01); *A61K 9/2072* (2013.01); *A61K 9/2077* (2013.01); *A61K 9/2866* (2013.01); *A61K 9/2886* (2013.01)

(58) Field of Classification Search
CPC .... A61K 31/65; A61K 9/2077; A61K 9/0053; A61K 9/2072; A61K 9/2886
See application file for complete search history.

(56) References Cited

U.S. PATENT DOCUMENTS

| 4,837,030 A | 6/1989 | Valorose, Jr. et al. |
| 5,262,173 A | 11/1993 | Sheth et al. |
| 5,277,916 A | 1/1994 | Dwyer et al. |
| 5,413,777 A * | 5/1995 | Sheth .................. A61K 9/5015 424/458 |

(Continued)

FOREIGN PATENT DOCUMENTS

| EP | 0 418 565 A2 | 3/1991 |
| GB | 2406517 A | 4/2005 |

(Continued)

OTHER PUBLICATIONS

Tobyn, et al.; "Physiochemical comparison between microcrystalline cellulose and silicified microcrystalline cellulose"; 1998; International Journal of Pharmaceutics; 169: 183-194.*

(Continued)

*Primary Examiner* — Timothy P Thomas
(74) *Attorney, Agent, or Firm* — Stites & Harbison, PLLC; Mandy Wilson Decker; Sean P. Ritchie

(57) ABSTRACT

The present application relates to a method of orally administering once daily tablet of minocycline to a subject in need thereof, wherein said tablet is substantially free of lactose. The present application also relates to processes for preparing said once daily tablet of minocycline that provides reduced stock keeping units with improved inventory by supplying multiple doses of minocycline in single tablet.

18 Claims, 5 Drawing Sheets

(56) References Cited

U.S. PATENT DOCUMENTS

| | | | |
|---|---|---|---|
| 5,908,838 A | 6/1999 | Gans | |
| 6,858,725 B1 * | 2/2005 | Vladyka, Jr. | A61K 9/2054 424/457 |
| 7,919,483 B2 | 4/2011 | Wortzman et al. | |
| 9,561,241 B1 | 2/2017 | Bakan et al. | |
| 2007/0003621 A1 * | 1/2007 | Nangia et al. | A61K 31/198 424/469 |

FOREIGN PATENT DOCUMENTS

| | | | |
|---|---|---|---|
| GB | 2414668 A | | 12/2006 |
| IN | 2008KO00236 A | * | 8/2009 |
| IN | 2008KO00236 A | * | 8/2009 |
| WO | 96/01623 A1 | | 1/1996 |
| WO | 20040078111 A2 | | 9/2004 |
| WO | 2007001961 A2 | | 1/2007 |
| WO | 2007002516 A2 | | 1/2007 |
| WO | 20080121107 A1 | | 10/2008 |
| WO | 20100046932 A2 | | 4/2010 |
| WO | 2013/092497 A1 | | 6/2013 |

OTHER PUBLICATIONS

Medicis Pharmaceutical Company; "Solydyn; NDA 050808"; https://www.accessdata.fda.gov/drugsatfda_docs/label/2011/050808s014lbl.pdf; 2011 revision (Year: 2011).*

Van Santen et al.; "Breaking of scored tablets: a review"; 2001; European Journal of Pharmaceutics and Biopharmaceutics; 53: 139-145 (Year: 2001).*

Moreton; "Sugar Spheres"; 2002; http://www.phexcom.com/Content/pdf/Sugar%20Spheres.pdf; accessed Feb. 14, 2020; pp. 630-631 (Year: 2002).*

Keny et al.; "Formulation and Evaluation of Once Daily Minocycline Hydrochloride Extended Release Matrix Tablets"; 2009; Indian J. Pharm. Sci.; 71(3):295-302 (Year: 2009).*

Plott R Todd et. al., "Key bioavailability features of a new extended-release formulation of minocycline hydrochloride tablets" Cutis, vol. 78, Issue 4 Suppl pp. 6-10 (2006).

European Patent Office, International Search Report cited in corresponding application No. PCT/IB2016/000553, dated Aug. 11, 2016.

Del Rosso, J.Q. Clinical Significance of Brand Versus Generic Formulations: Focus on Oral Minocycline. Cutis, 2006, 77(3): 153-156.

Leyden, J.J., et al. Oral Antibiotic Therapy for Acne Vulgaris Pharmacokinetic and Pharmacodynamic Perspectives. J. Clin. Aesthet. Dermatol, 2011, 4(2):40-47.

XIMINO Prescribing Information (Jul. 2012).

Pan, S, et al. Weight-based dosing in medication use: what should we know? Patient Prefer Adherence, 10:549-560, 2016.

Vranic, E., et al. Influence of Tablet Splitting on Content Uniformity of Lisinopril/Hydrochlorthiazide Tablets. Bosn J. Basic Med Sci. 2007, 7(4):328-334.

Mandal, T.K. Effect of tablet integrity on the dissolution rate of sustained-release preparations. J Clin Pharm Ther. Jun. 1996, 21(3):155-7.

Trivedi, M.R., et al. A Review on Tablet Scoring: Background, History and Current Regulatory Considerations. J. Pharm Res. Intl, 2017, 20(5):1-7.

* cited by examiner

PHARMACEUTICAL COMPOSITIONS FOR MINOCYCLINE

RELATED APPLICATIONS

This application claims priority from Indian Provisional Application No. 1815/CHE/2015, filed Apr. 7, 2015, the entire disclosure of which is incorporated herein by this reference.

TECHNICAL FIELD

The present invention relates to a composition comprising minocycline, a method of orally administering a once daily tablet of minocycline to a subject in need thereof, and a processes for preparing the tablet thereof.

BACKGROUND

Minocycline is a semi synthetic derivative of tetracycline, [4S-(4α,4aα,5aα,12aα)]-4,7-Bis(dimethylamino)-1,4,4a,5,5a,6,11,12a-octahydro-3,10,12,12a-tetrahydroxy-1,11-dioxo-2-naphthacenecarboxamide. The Orange Book of USFDA lists various dosage forms of minocycline hydrochloride such as immediate release (IR) tablets, capsules, and extended release (ER) tablets, indicated for the treatment of only inflammatory lesions of non-nodular moderate to severe acne vulgaris in subjects 12 years of age and older. Intravenous injection is available for the treatment of infections caused by various bacteria. Additionally, extended release powder for dental applications is available for treatment as an adjunct to scaling and root planning procedures for reduction of pocket depth in subjects with adult periodontitis.

Acne is a common skin condition affecting people at some point during their lives. Severe acne is inflammatory and often caused by infection due to one or more bacterial species. Oral antibiotics are a mainstay in the treatment of acne. Minocycline is among one such antibiotic, absorbed at different rates in different portions of the gastrointestinal tract. Conventional dosage forms containing minocycline require frequent ingestion of multiple doses per day, resulting in wide variations in serum concentration throughout the course of treatment and some subjects experiencing vestibular adverse effects with immediate release oral dosage forms. Such downsides relating to minocycline dosage forms ultimately lead to reduced rates of subject compliance. Currently in the USA, SOLODYN® is available as once daily dosage form of minocycline that provides antibiotically effective dose of approximately 1 milligram per kilogram of body weight (1 mg/kg) for treating acne.

In the past, various attempts have been made to prepare modified release oral dosage forms of minocycline for the treatment of acne. In particular:

U.S. Pat. No. 4,837,030 from American Cyanamid Company relates to a minocycline dosage form that retards release in stomach and promotes rapid release in intestine. The dosage form is prepared by using ultrathin layer of a polymer particularly ethyl cellulose and hydroxy propyl methyl cellulose.

U.S. Pat. No. 5,908,838 from Medicis relates to a slowly dissolving dosage form for oral tetracycline class antibiotics, including minocycline, which results in the reduction of vestibular side effects.

U.S. Pat. No. 5,262,173 from American Cyanamid Company relates to pulsatile once daily capsule dosage form of minocycline comprising granules, which are coated with pH sensitive or pH non-sensitive polymers to provide slow release in pH about 1.0 to about 3.0 and rapid release in a medium having a pH about 4.5 to about 6.5, which are administered simultaneously.

U.S. Pat. No. 5,413,777 from American Cyanamid Company relates to pulsatile once daily capsule dosage form of minocycline comprising granules, which are coated with pH sensitive or pH non-sensitive polymers to provide rapid release in a medium having a pH of less than about 3.9 and slow release in a medium having a pH from about 4.0 to about 7.5, which are administered either simultaneously or separately up to about 120 minutes apart.

U.S. Pat. No. 5,277,916 from F. H. Faulding & Co Ltd. relates to a tetracycline pharmaceutical composition comprising a plurality of coated core in a pellet form, which is partially soluble at an acidic pH and provides release more slowly in the stomach than in the intestine.

U.S. Pat. No. 7,919,483 from Medicis Pharm Corp. relates to a method of treating acne vulgaris, comprising administering a continuous slow release oral dosage form comprising a delivery vehicle having lactose monohydrate, that provides 0.7 mg/kg/day to 1.3 mg/kg/day of said oral minocycline antibiotic to the subject, once daily without a loading dose.

PCT application no. WO 2004/078111 A2 from Ranbaxy Labs Ltd. relates to extended release minocycline compositions comprising two or more hydrophilic matrix forming polymers having different viscosity.

Despite the availability of prior art dosage forms of minocycline for the treatment of acne, there remains a need for treating acne that provides once daily composition for effective administration of appropriate dose of minocycline. SOLODYN® doesn't provide flexibility of dosing especially to subjects having swallowing disability such as dysphagia. Additionally, it contains lactose which is highly reactive due to its hemiacetal structure and which can eventually cause chemical instability with active components. Further, due to the solubility of minocycline of around 50 mg/ml, the drug has extremely poor binding affinity towards pharmaceutically acceptable excipients and hence, to provide a predictable and accurate fractional dose is difficult.

Presently, in the USA, SOLODYN® or its generic versions are supplied in 8 strengths—45, 55, 65, 80, 90, 105, 115 & 135 mg of minocycline containing oral tablets, packaged in individual units (otherwise known as "Stock keeping Unit" or "SKU"). These different units (having different strengths) are supplied to cater the need of subjects with body weight from 45 kg to 135 kg. However, handling these many units (SKU) is cumbersome in manufacturing, supply chain, inventory and for chemists. Further, it would be advantageous to have reduced number of "Stock Keeping Units (SKUs)", in order to improve the inventory in pharmacy, warehouse—drug storage or in supply chain.

SUMMARY OF THE INVENTION

Accordingly, the present application relates to a method of orally administering a once daily tablet of minocycline to a subject. The tablet is substantially free of reactive excipients like lactose or its pharmaceutically acceptable hydrates, hemihydrates or anhydrous forms, and can be administered to subjects having lactose intolerance. Additionally, the tablet can be administered by dispersion into food, which provides subject compliance especially to those suffering from dysphagia.

The present application also relates to a tablet of minocycline or a pharmaceutically acceptable salt thereof, which is free of lactose or substantially free of lactose. The present tablets of minocycline also comprises one or more score(s) or separation mark(s) for dividing the tablet into equal subunits and provides efficient processes for preparation thereof, wherein a supply of said tablet reduces SKUs by at least 50%.

In an embodiment, the present application relates to a pharmaceutical composition of minocycline.

In another embodiment, the present application relates to a pharmaceutical composition of minocycline, comprising minocycline and one or more pharmaceutically acceptable excipient(s), wherein said composition comprises (i) an immediate release (IR) portion and (ii) an extended release (ER) portion.

In yet another embodiment, the present application relates to a pharmaceutical composition of minocycline, comprising minocycline and one or more pharmaceutically acceptable excipient(s), wherein said composition comprises (i) about 20 to about 40 percent of minocycline in an immediate release (IR) portion and (ii) about 80 to about 60 percent of minocycline in an extended release (ER) portion.

In an embodiment, the present application relates to a once daily tablet of minocycline, wherein said tablet is substantially free of lactose.

In another embodiment, the present application relates to a once daily tablet of minocycline, comprising minocycline and one or more pharmaceutically acceptable excipient(s), wherein said tablet comprises (i) an immediate release (IR) portion and (ii) an extended release (ER) portion.

In yet another embodiment, the present application relates to a once daily tablet of minocycline, comprising minocycline and one or more pharmaceutically acceptable excipient(s), wherein said tablet comprises (i) about 20 to about 40 percent of minocycline in an immediate release (IR) portion and (ii) about 80 to about 60 percent of minocycline in an extended release (ER) portion.

In an aspect of the above embodiments, the tablet of the present application comprises an immediate release (IR) portion and an extended release (ER) portion present in a ratio of about 20:80 to about 40:60.

In an aspect of the above embodiments, the tablet of the present application comprises one or more cushioning agent(s) that provides cushion effect during the compression and fills the void space to prevent adhesion and fusion of coated release portions during compression.

The amount of one or more cushioning agents that may be used in the present application ranges from about 40% to about 60% by weight of the present tablets.

In one embodiment, the composition of the present application exhibits at least one of the following dissolution profiles when measured in USP type I apparatus at 100 rpm in 900 ml of simulated gastric fluid with a pH of 2.1 and at 37° C.: about 15% to about 25% of minocycline in 15 minutes, about 35% to about 50% of minocycline in 30 minutes, about 50% to about 65% of minocycline in 60 minutes, and about 70% to about 90% of minocycline in 120 minutes.

In yet another aspect of the above embodiments, the tablet of the present application comprises at least one score or other means of separation mark(s) for dividing the tablet into two or more equal subunits to provide a predictable and accurate fractional dose of minocycline, wherein said divided subunits have uniformity of drug content.

In an aspect of the above embodiments, the tablet of the present application is administered as intact or by dividing into two or more equal subunits to provide a predictable and accurate fractional dose of minocycline.

In an embodiment, the present application relates to a once daily oral tablet of minocycline comprising 90 mg, 105 mg, 115 mg, 135 mg or 165 mg of minocycline, wherein said tablet comprises (i) an immediate release (IR) portion, (ii) an extended release (ER) portion, and (iii) one or more pharmaceutically acceptable excipients, and said tablet is substantially free of lactose.

In another embodiment, the present application relates to a method of treating acne in a subject comprising orally administering a once daily tablet of minocycline, wherein said tablet is substantially free of lactose.

In an aspect of the above embodiments, the tablet of the present application comprises (i) about 20 to about 40 percent of minocycline in an immediate release (IR) portion, (ii) about 80 to about 60 percent of minocycline in an extended release (ER) portion, and (iii) one or more pharmaceutically acceptable excipients.

In an embodiment, the present application relates to a method of orally administering once daily tablet of minocycline comprising 90 mg, 105 mg, 115 mg, 135 mg or 165 mg of minocycline, wherein said tablet comprises (i) about 20 to about 40 percent of minocycline in an immediate release (IR) portion, (ii) about 80 to about 60 percent of minocycline in an extended release (ER) portion, and (iii) one or more pharmaceutically acceptable excipients, and said tablet is substantially free of lactose.

In an aspect of the above embodiments, the immediate release (IR) portion comprises about 18 mg to about 66 mg of minocycline.

In an aspect of the above embodiments, the extended release (ER) portion comprises about 54 mg to about 132 mg of minocycline.

In an aspect of the above embodiments, the tablet of the present application has at least one score or other means of separation mark(s) for dividing the tablet into two or more equal subunits to provide a predictable and accurate fractional dose of minocycline, wherein said divided subunits have uniformity of drug content and provide a dose of about 0.5-1.5 mg/kg/day or about 0.7-1.3 mg/kg/day or about 1 mg/kg/day.

In another aspect of the above embodiments, the tablet comprising 90 mg of minocycline is dispensed as intact to subjects having body weight of 81-96 kg or divided into two equal subunits, wherein each subunit provides 45 mg strengths of minocycline and dispensed to subjects having body weight of 40-49 kg.

In another aspect of the above embodiments, the tablet comprising 105 mg of minocycline is dispensed as intact to subjects having body weight of 85-110 kg, divided into two equal subunits of 52.5 mg strengths of minocycline and dispensed to subjects having body weight of 45-59 kg, or divided into three equal subunits of 35 mg strengths of minocycline and dispensed to subjects having body weight of 35-39 kg.

In another aspect of the above embodiments, the tablet comprising 135 mg of minocycline dispensed as intact to subjects having body weight of 111-136 kg, divided into two equal subunits of 67.5 mg strengths of minocycline and dispensed to subjects having body weight of 60-84 kg, or divided into three equal subunits of 45 mg strengths of minocycline and dispensed to subjects having body weight of 40-49 kg.

In another aspect of the above embodiments, the tablet comprising 165 mg of minocycline dispensed as intact to subjects having body weight of 146-165 kg, divided into two equal subunits of 82.5 mg strengths of minocycline and dispensed to subjects having body weight of 80-88 kg, or divided into three equal subunits of 55 mg strength of minocycline and dispensed to subjects having body weight of 50-59 kg.

In an embodiment, the present application relates to an once daily oral tablet of minocycline, comprising 35 mg, 45 mg, 52.5 mg, 55 mg, 57.5 mg, 67.5 mg, 70 mg, 82.5 mg, 90 mg, 105 mg, 110 mg, 115 mg, 135 mg or 165 mg of minocycline, wherein said tablet comprises (i) an immediate release (IR) portion and (ii) an extended release (ER) portion, said tablet is substantially free of lactose, and said tablet exhibits at least one of the following dissolution profile when measured in USP type I apparatus at 100 rpm in 900 ml of simulated gastric fluid with a pH of 2.1 and at 37° C.: about 15% to about 25% of minocycline in 15 minutes, about 35% to about 50% of minocycline in 30 minutes, about 50% to about 65% of minocycline in 60 minutes, and about 70% to about 90% of minocycline in 120 minutes.

In one embodiment, the composition of the present application exhibits at least one of the following dissolution profile when measured in USP type I apparatus at 100 rpm in 900 ml of acetate buffer with a pH of 4.5 and at 37° C.: about 15% to about 25% of minocycline in 15 minutes, about 35% to about 45% of minocycline in 30 minutes, about 50% to about 65% of minocycline in 60 minutes, and about 70% to about 90% of minocycline in 120 minutes In one embodiment, the composition of the present application exhibits at least one of the following dissolution profile when measured in USP type I apparatus at 100 rpm in 900 ml of phosphate buffer with a pH of 5.5 and at 37° C.: about 15% to about 25% of minocycline in 15 minutes, about 35% to about 45% of minocycline in 30 minutes, about 50% to about 65% of minocycline in 60 minutes, and about 70% to about 90% of minocycline in 120 minutes In another embodiment, the present application relates to an once daily oral tablet of minocycline, comprising 90 mg, 105 mg, 115 mg, 135 mg or 165 mg of minocycline, wherein said tablet is substantially free of lactose, said tablet exhibits bioequivalence to a corresponding SOLODYN® tablet when administered to healthy human subjects in fasting and fed conditions, and said bioequivalence is established by: (a) a 90% Confidence Interval for mean $C_{max}$, which is between 80% and 125%, (b) a 90% Confidence Interval for mean $AUC_{(0-t)}$, which is between 80% and 125%, and (c) a 90% Confidence Interval for mean $AUC_{(0-\infty)}$, which is between 80% and 125%.

In another embodiment, the present application relates to a once daily oral tablet of minocycline comprising 90 mg, 105 mg, 115 mg, 135 mg, or 165 mg of minocycline, wherein said tablet comprises at least one score or other means of separation mark(s) for dividing the tablet into two or more equal subunits, to provide at least 50% reduced stock keeping units in a pharmacy or warehouse.

In an aspect of the above embodiment, the tablet of the present application is dispensed as intact or by dividing into two or more equal subunits to provide a minocycline dose of approximately 1 mg/kg body weight to a subject for treating acne.

In an aspect of the above embodiments, the tablet of the present application comprising 90 mg, 105 mg, 115 mg, 135 mg or 165 mg of minocycline provides inventory optimization to a pharmacy or a warehouse for said strengths of minocycline.

In an aspect of the above embodiments, the tablet of the present application comprising 90 mg of minocycline provides inventory optimization to a pharmacy or a warehouse by providing 45 mg or 90 mg strengths of minocycline in scored tablets.

In an aspect of the above embodiments, the tablet of the present application comprising 105 mg of minocycline provides inventory optimization to a pharmacy or a warehouse by providing 35 mg, 52.5 mg or 105 mg strengths of minocycline in scored tablets.

In an aspect of the above embodiments, the tablet of the present application comprising 135 mg of minocycline provides inventory optimization to a pharmacy or a warehouse by providing 45 mg, 67.5 mg or 135 mg strengths of minocycline in scored tablets.

In an aspect of the above embodiments, the tablet of the present application comprising 165 mg of minocycline provides inventory optimization to a pharmacy or a warehouse by providing 55 mg, 82.5 mg or 165 mg strengths of minocycline in scored tablets.

In an aspect of the above embodiments, the minocycline is minocycline hydrochloride.

In one aspect, the compositions of the present application are substantially free of lactose.

In one aspect, the compositions of the present application are administered for the treatment of acne.

DETAILED DESCRIPTION OF THE INVENTION

Figure 1:
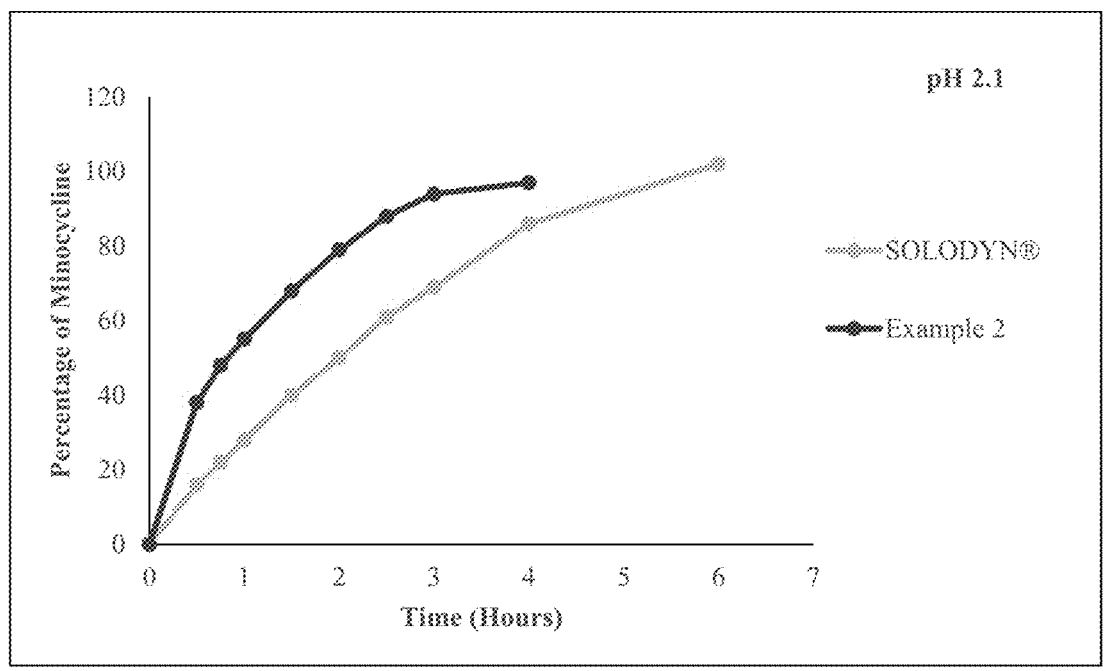
FIG. 1 shows in-vitro release profile for example 2 and SOLODYN® in 900 ml of pH 2.1 Simulated Gastric Fluid, USP Type 1 apparatus at a speed of 100 rpm.

The details of one or more embodiments of the present invention are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Definitions: The terms as used herein have the following meanings:

The present invention can comprise or consist essentially of the components of the present invention as well as other ingredients or elements described herein. As used herein, "comprising" means the elements recited, or their equivalent in structure or function, plus any other element or elements which are not recited. The terms "having," "including," and "comprised of" are also to be construed as open ended unless the context suggests otherwise. As used herein, "consisting essentially of" means that the invention may include ingredients in addition to those recited in the claim, but only if the additional ingredients do not materially alter the basic and novel characteristics of the claimed invention.

The terms "a" and "the" as used herein, are understood to encompass the plural as well as the singular or otherwise clearly mentioned wherever needed. For example, reference to "an excipient" includes reference to one or more of such excipients, and reference to "the vehicle" includes reference to one or more of such vehicles.

The terms "about," "up to," "generally," and the like are to be construed as modifying a term or value such that it is not an absolute. Such terms will be defined by the circumstances and the terms that they modify as those terms are understood by those of skill in the art. This includes, at very least, the degree of expected experimental error, technical error and instrumental error for a given experiment, technique or an instrument used to measure a value. The term "about" is used to provide flexibility to a numerical range endpoint by providing that a given value may be "a little above" or "a little below" the endpoint. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum.

The terms "composition" and "formulation" refer to a mixture of two or more compounds, elements, or molecules. Also this term may be used to refer to a mixture of one or more active agents with a pharmaceutically acceptable vehicle or excipients. Furthermore, the term "dosage form" can include one or more formulation(s) or composition(s) provided in a format for administration like tablets, capsules, pills, minitablets, pellets, granules, powder and the like or mixtures thereof.

The term "substantially free of lactose" as used herein, refers to a pharmaceutical composition of present application that has less than about 5%, 3%, 2%, 1%, or 0.5% w/w of lactose or pharmaceutically acceptable hydrates, hemihydrates, or anhydrous forms thereof by weight of the present pharmaceutical composition, while formulating or in storage of the composition.

The term "SOLODYN®" is used to represent extended release oral tablets of minocycline or its pharmaceutical equivalents or its therapeutic equivalents or later approved drugs which are designated as AB rated by US FDA as per Approved Drug Products with Therapeutic Equivalence Evaluations (34$^{th}$ edition) or drugs obtained marketing approval by US FDA through Abbreviated New Drug Application (ANDA) filing by establishing bioequivalence to such Product. For example, in some embodiments, SOLODYN® includes minocycline hydrochloride along with excipients such as lactose monohydrate NF, hypromellose type 2910 USP, magnesium stearate NF, colloidal silicon dioxide NF, and carnauba wax NF. In some embodiments SOLODYN® includes its US FDA approved therapeutic or pharmaceutical equivalents. SOLODYN® is a Trademark registered and owned by Medicis Pharmaceutical Corporation Delaware 7720 North Dobson Road Scottdale Arizona 85256.

The term "minocycline" as used herein, is intended to include, but not limited to, minocycline and pharmaceutically acceptable, pharmacologically active derivatives of minocycline, including both individual enantiomers of minocycline (dextrogyral and levogyral enantiomers) in their substantially pure form and their pharmaceutically acceptable salts, mixtures (in any ratio) of minocycline enantiomers and their pharmaceutically acceptable salts, and active metabolites of minocycline and their pharmaceutically acceptable salts. The chemical formulation of minocycline is [4S-(4α,4aα,5aα,12aα)]-4,7-Bis(dimethylamino)-1,4,4a,5,5a,6,11,12a-octahydro-3,10,12,12a-tetrahydroxy-1,11-dioxo-2-naphthacenecarboxamide. The solid state form of minocycline used in the composition is not critical. For example, minocycline can be amorphous or crystalline.

The term "pharmaceutically acceptable salts" as used herein, includes those salts which are, within the scope of sound medical judgment, suitable for use in contact with the tissues of humans and lower animals without undue toxicity, irritation, allergic response and the like, which are well known in the art. The salts can be prepared in situ during the final isolation and purification of the compounds of the invention, or separately by reacting the pharmaceutically active substance having a free base function with a suitable organic acid or inorganic acid. Examples of pharmaceutically acceptable salts include, but are not limited to, any of the salts or co-crystals of minocycline selected from hydrochloride, hydrobromide, sulphate, citrate, phosphate, maleate, formate, acetate, nitrate, mesylate, succinate, benzoate and the like. The salts may be in the form of solvate, hydrate, hemihydrates, or anhydrous forms.

The term "dose" as used herein, means a prescribed amount of minocycline which is sufficient for the treatment of acne, but low enough to avoid serious side effects (at a reasonable benefit/risk ratio), within the scope of sound medical judgment. The effective amount of the minocycline will vary with the particular condition being treated, the age and physical condition of the subject being treated, the severity of the condition, the duration of the treatment, the nature of concurrent therapy, and like factors within the knowledge and expertise of the attending physician.

The term "extended release" as used herein, refers to composition or dosage form of minocycline which is formulated to provide a longer duration of pharmacological response after administration of the dosage form than is ordinarily experienced after administration of a corresponding immediate release composition. Extended release compositions include, inter alia, those compositions described elsewhere as "controlled release", "modified release", "delayed release", "sustained release", "prolonged release", "programmed release", "slow release" "time release" and/or "rate controlled" compositions or dosage forms.

The term, "acne" as used herein, refers to various skin conditions characterized by papules, pustules, cysts, nodules, comedones, and other blemishes or skin lesions. For the purposes of this specification, acne means all known types of acne comprising superficial acne, low grade acne, pre-acne or acne lesions which includes, but are not limited to, acne vulgaris, cystic acne, acne atrophica, bromide acne, chlorine acne, acne conglobata, acne cosmetica, acne detergicans, epidemic acne, acne estivalis, acne fulminans, halogen acne, acne indurata, iodide acne, acne keloid, acne mechanica, acne papulosa, pomade acne, premenstral acne, acne pustulosa, acne scorbutica, acne scrofulosorum, acne urticata, acne varioliformis, acne venenata, propionic acne, acne excoriee, gram negative acne, steroid acne, nodulocystic acne and acne rosacea.

The term, "dysphagia" as used herein, refers to collective term which includes swallowing problems such as difficulty in swallowing, inability to swallow or discomfort in swallowing or related difficulties.

The term "food dispersion" covers an edible food product in the form of aqueous dispersion having semi-solid consistency, selected from the group comprising of applesauce, puree, jam, food syrups and the like or mixtures thereof.

The term "stable" as used herein, refers to chemical and physical stability of the present tablets of minocycline when stored at 25° C. and 60% Relative Humidity (RH) for at least 12 months or at 40° C. and 75% Relative Humidity (RH) for 6 months or when allowed to disperse in food dispersion for at least one hour.

The term "subject" as used herein refers to a human individual suffering from acne, who is to be a recipient of the present pharmaceutical composition of minocycline.

As used herein, the terms "optional" or "optionally" mean that the subsequently described event or circumstance does or does not occur or exist and that the description includes instances where said event or circumstance occurs or exists, and instances where it does not.

As used herein, the terms "treatment" or "treating" relate to curing or substantially curing a condition, as well as ameliorating at least one symptom of the condition, and are inclusive of prophylactic treatment and therapeutic treatment. As would be recognized by one or ordinary skill in the art, treatment that is administered prior to clinical manifestation of a condition then the treatment is prophylactic (i.e., it protects the subject against developing the condition). If the treatment is administered after manifestation of the condition, the treatment is therapeutic (i.e., it is intended to diminish, ameliorate, control, or maintain the existing condition and/or side effects associated with the condition). The terms relate to medical management of a subject with the intent to substantially cure, ameliorate, stabilize, or substantially prevent a condition, including but not limited to prophylactic treatment to preclude, avert, obviate, forestall, stop, or hinder something from happening, or reduce the severity of something happening, especially by advance action. As such, the terms treatment or treating include, but are not limited to: inhibiting the progression of a condition of interest; arresting or preventing the development of a condition of interest; reducing the severity of a condition of interest; ameliorating or relieving symptoms associated with a condition of interest; causing a regression of the condition of interest or one or more of the symptoms associated with the condition of interest; and preventing a condition of interest or the development of a condition of interest.

In an embodiment, the present application relates to a pharmaceutical composition of minocycline.

In an embodiment, the present application relates to a method of orally administering pharmaceutical composition of minocycline to a subject in need thereof.

In another embodiment, the present application relates to a pharmaceutical composition of minocycline, comprising minocycline and one or more pharmaceutically acceptable excipient(s), wherein said composition comprises (i) an immediate release (IR) portion and (ii) an extended release (ER) portion.

In yet another embodiment, the present application relates to a pharmaceutical composition of minocycline, comprising minocycline and one or more pharmaceutically acceptable excipient(s), wherein said composition comprises (i) about 20 to about 40 percent of minocycline in an immediate release (IR) portion and (ii) about 80 to about 60 percent of minocycline in an extended release (ER) portion.

In an aspect of the above embodiments, the IR and ER portions are present in a ratio of about 20:80 to about 40:60.

In an embodiment, the present application relates to a pharmaceutical composition of minocycline, comprising minocycline and one or more pharmaceutically acceptable excipient(s), wherein said composition comprises (i) an immediate release (IR) portion and (ii) an extended release (ER) portion, present in a ratio of about 20:80 to about 40:60.

In yet another embodiment, the present application relates to a pharmaceutical composition of minocycline, comprising minocycline and one or more pharmaceutically acceptable excipient(s), wherein said composition comprises (i) about 20 to about 40 percent of minocycline in an immediate release (IR) portion and (ii) about 80 to about 60 percent of minocycline in an extended release (ER) portion, present in a ratio of about 20:80 to about 40:60.

In an aspect of the above embodiments, the present pharmaceutical composition of minocycline includes, but are not limited to, tablets, capsules, pills, minitablets, pellets, granules, powder and the like or mixtures thereof.

In an embodiment, the compositions of the present application are substantially free of lactose.

In an embodiment, the present application relates to a method of orally administering once daily tablet of minocycline to a subject in need thereof.

In another embodiment, the present application relates to a once daily tablet of minocycline, comprising minocycline and one or more pharmaceutically acceptable excipient(s), wherein said tablet comprises (i) an immediate release (IR) portion and (ii) an extended release (ER) portion.

In yet another embodiment, the present application relates to a method of orally administering once daily tablet of minocycline, to a subject in need thereof, comprising minocycline and one or more pharmaceutically acceptable excipient(s), wherein said tablet comprises (i) an immediate release (IR) portion and (ii) an extended release (ER) portion.

In yet another embodiment, the present application relates to a once daily tablet of minocycline, comprising minocycline and one or more pharmaceutically acceptable excipient(s), wherein said tablet comprises (i) about 20 to about 40 percent of minocycline in an immediate release (IR) portion and (ii) about 80 to about 60 percent of minocycline in an extended release (ER) portion.

In yet another embodiment, the present application relates to a method of orally administering once daily tablet of minocycline to a subject in need thereof, comprising minocycline and one or more pharmaceutically acceptable excipient(s), wherein said tablet comprises (i) about 20 to about 40 percent of minocycline in an immediate release (IR) portion and (ii) about 80 to about 60 percent of minocycline in an extended release (ER) portion.

In another aspect of the above embodiments, the IR and ER portions are present in a ratio of about 20:80 to about 40:60.

In an embodiment, the present application relates to a once daily tablet of minocycline, comprising minocycline and one or more pharmaceutically acceptable excipient(s), wherein said tablet comprises (i) an immediate release (IR) portion and (ii) an extended release (ER) portion, present in a ratio of about 20:80 to about 40:60.

In another embodiment, the present application relates to a method of orally administering once daily tablet of minocycline to a subject in need thereof, comprising minocycline and one or more pharmaceutically acceptable excipient(s), wherein said tablet comprises (i) an immediate release (IR)

portion and (ii) an extended release (ER) portion, present in a ratio of about 20:80 to about 40:60.

In yet another embodiment, the present application relates to a once daily tablet of minocycline, comprising minocycline and one or more pharmaceutically acceptable excipient(s), wherein said tablet comprises (i) about 20 to about 40 percent of minocycline in an immediate release (IR) portion and (ii) about 80 to about 60 percent of minocycline in an extended release (ER) portion, present in a ratio of about 20:80 to about 40:60.

In yet another embodiment, the present application relates to a method of orally administering once daily tablet of minocycline to a subject in need thereof, comprising minocycline and one or more pharmaceutically acceptable excipient(s), wherein said tablet comprises (i) about 20 to about 40 percent of minocycline in an immediate release (IR) portion and (ii) about 80 to about 60 percent of minocycline in an extended release (ER) portion, present in a ratio of about 20:80 to about 40:60.

In another embodiment, the tablet used in the method of administration is substantially free of lactose.

In an embodiment, the present application relates to a method of treating acne administering a pharmaceutical composition of minocycline.

In another embodiment, the present application relates to a method of treating acne administering a pharmaceutical composition of minocycline, comprising minocycline and one or more pharmaceutically acceptable excipient(s), wherein said composition comprises (i) an immediate release (IR) portion and (ii) an extended release (ER) portion.

In yet another embodiment, the present application relates to a method of treating acne administering a pharmaceutical composition of minocycline, comprising minocycline and one or more pharmaceutically acceptable excipient(s), wherein said composition comprises (i) about 20 to about 40 percent of minocycline in an immediate release (IR) portion and (ii) about 80 to about 60 percent of minocycline in an extended release (ER) portion.

In an aspect of the above embodiments, the IR and ER portions are present in a ratio of about 20:80 to about 40:60.

In an embodiment, the present application relates to a method of treating acne administering a pharmaceutical composition of minocycline, comprising minocycline and one or more pharmaceutically acceptable excipient(s), wherein said composition comprises (i) an immediate release (IR) portion and (ii) an extended release (ER) portion, present in a ratio of about 20:80 to about 40:60.

In yet another embodiment, the present application relates to a method of treating acne administering a pharmaceutical composition of minocycline, comprising minocycline and one or more pharmaceutically acceptable excipient(s), wherein said composition comprises (i) about 20 to about 40 percent of minocycline in an immediate release (IR) portion and (ii) about 80 to about 60 percent of minocycline in an extended release (ER) portion, present in a ratio of about 20:80 to about 40:60.

In an aspect of the above embodiments, the present pharmaceutical composition of minocycline includes, but are not limited to, tablets, capsules, pills, minitablets, pellets, granules, powder and the like or mixtures thereof In an embodiment, the compositions of the present application are substantially free of lactose.

In an aspect of the above embodiments, the immediate release (IR) and/or extended release (ER) portions are present in the form of a granule, pellet, bead, spherule, powder and the like or mixtures thereof.

In an aspect of the above embodiments, a once daily tablet of minocycline of the present application comprises one or more cushioning agent(s) that provides cushion effect during the compression and fills the void space to prevent adhesion and fusion of coated release portions during compression.

Suitable examples of one or more such cushioning agents used in the present application, which include, but are not limited to, microcrystalline cellulose, silicified microcrystalline cellulose, calcium phosphate, mannitol, sorbitol, polyethylene glycol, sodium stearyl fumarate, magnesium stearate, starch, talc or mixtures thereof.

The amount of one or more cushioning agents that may be used in the present application ranges from about 40% to about 60% by weight of the present tablets.

In yet another aspect of the above embodiments, a once daily tablet of minocycline of the present application comprises immediate release (IR) and extended release (ER) portions, and one or more cushioning agent(s), wherein said release portions are present with said cushioning agent(s) in a ratio of from about 40:60 to about 50:50.

In an embodiment, the present application relates to a once daily tablet of minocycline comprising minocycline and one or more cushioning agent(s), wherein said tablet comprises (i) an immediate release (IR) portion and (ii) an extended release (ER) portion, and wherein said release portions are present with said cushioning agent(s) in a ratio of from about 40:60 to about 50:50.

In one embodiment, the present application relates to a method of orally administering once daily tablet of minocycline to a subject in need thereof, comprising minocycline and one or more cushioning agent(s), wherein said tablet comprises (i) an immediate release (IR) portion and (ii) an extended release (ER) portion, and wherein said release portions are present with said cushioning agent(s) in a ratio of from about 40:60 to about 50:50.

In another embodiment, the present application relates to a once daily tablet of minocycline comprising minocycline and one or more cushioning agent(s), wherein said tablet comprises (i) about 20 to about 40 percent of minocycline in an immediate release (IR) portion and (ii) about 80 to about 60 percent of minocycline in an extended release (ER) portion, and wherein said release portions are present with said cushioning agent(s) in a ratio of from about 40:60 to about 50:50.

In another embodiment, the present application relates to a method of orally administering once daily tablet of minocycline to a subject in need thereof, comprising minocycline and one or more cushioning agent(s), wherein said tablet comprises (i) about 20 to about 40 percent of minocycline in an immediate release (IR) portion and (ii) about 80 to about 60 percent of minocycline in an extended release (ER) portion, and wherein said release portions are present with said cushioning agent(s) in a ratio of from about 40:60 to about 50:50.

In an embodiment, the present application relates to a once daily oral tablet of minocycline, comprising minocycline and one or more pharmaceutically acceptable excipient(s), comprising (i) an immediate release (IR) portion and (ii) an extended release (ER) portion and said tablet exhibits at least one of the following dissolution profile when measured in USP type I apparatus at 100 rpm in 900 ml of simulated gastric fluid with a pH of 2.1 and at 37° C.: about 15% to about 25% of minocycline in 15 minutes, about 35% to about 50% of minocycline in 30 minutes, about 50% to about 65% of minocycline in 60 minutes, and about 70% to about 90% of minocycline in 120 minutes.

In another embodiment, the present application relates to a once daily oral tablet of minocycline, comprising minocycline and one or more pharmaceutically acceptable excipient(s), comprising (i) about 20 to about 40 percent of minocycline in an immediate release (IR) portion and (ii) about 80 to about 60 percent of minocycline in an extended release (ER) portion and said tablet exhibits at least one of the following dissolution profile when measured in USP type I apparatus at 100 rpm in 900 ml of simulated gastric fluid with a pH of 2.1 and at 37° C.: about 15% to about 25% of minocycline in 15 minutes, about 35% to about 50% of minocycline in 30 minutes, about 50% to about 65% of minocycline in 60 minutes, and about 70% to about 90% of minocycline in 120 minutes.

In an embodiment, the present application relates to a once daily oral tablet of minocycline, comprising minocycline and one or more pharmaceutically acceptable excipient(s), comprising (i) an immediate release (IR) portion and (ii) an extended release (ER) portion and said tablet exhibits at least one of the following dissolution profile when measured in USP type I apparatus at 100 rpm in 900 ml of acetate buffer with a pH of 4.5 and at 37° C.: about 15% to about 25% of minocycline in 15 minutes, about 35% to about 45% of minocycline in 30 minutes, about 50% to about 65% of minocycline in 60 minutes, and about 70% to about 90% of minocycline in 120 minutes.

In another embodiment, the present application relates to a once daily oral tablet of minocycline, comprising minocycline and one or more pharmaceutically acceptable excipient(s), comprising (i) about 20 to about 40 percent of minocycline in an immediate release (IR) portion and (ii) about 80 to about 60 percent of minocycline in an extended release (ER) portion and said tablet exhibits at least one of the following dissolution profile when measured in USP type I apparatus at 100 rpm in 900 ml of acetate buffer with a pH of 4.5 and at 37° C.: about 15% to about 25% of minocycline in 15 minutes, about 35% to about 45% of minocycline in 30 minutes, about 50% to about 65% of minocycline in 60 minutes, and about 70% to about 90% of minocycline in 120 minutes.

In an embodiment, the present application relates to a once daily oral tablet of minocycline, comprising minocycline and one or more pharmaceutically acceptable excipient(s), comprising (i) an immediate release (IR) portion and (ii) an extended release (ER) portion and said tablet exhibits at least one of the following dissolution profile when measured in USP type I apparatus at 100 rpm in 900 ml of phosphate buffer with a pH of 5.5 and at 37° C.: about 15% to about 25% of minocycline in 15 minutes, about 35% to about 45% of minocycline in 30 minutes, about 50% to about 65% of minocycline in 60 minutes, and about 70% to about 90% of minocycline in 120 minutes.

In another embodiment, the present application relates to a once daily oral tablet of minocycline, comprising minocycline and one or more pharmaceutically acceptable excipient(s), comprising (i) about 20 to about 40 percent of minocycline in an immediate release (IR) portion and (ii) about 80 to about 60 percent of minocycline in an extended release (ER) portion and said tablet exhibits at least one of the following dissolution profile when measured in USP type I apparatus at 100 rpm in 900 ml of phosphate buffer with a pH of 5.5 and at 37° C.: about 15% to about 25% of minocycline in 15 minutes, about 35% to about 45% of minocycline in 30 minutes, about 50% to about 65% of minocycline in 60 minutes, and about 70% to about 90% of minocycline in 120 minutes.

In an embodiment, the present application relates to a method of orally administering once daily tablet of minocycline to a subject in need thereof, comprising minocycline and one or more pharmaceutically acceptable excipient(s), comprising (i) an immediate release (IR) portion and (ii) an extended release (ER) portion and said tablet exhibits at least one of the following dissolution profile when measured in USP type I apparatus at 100 rpm in 900 ml of simulated gastric fluid with a pH of 2.1 and at 37° C.: about 15% to about 25% of minocycline in 15 minutes, about 35% to about 50% of minocycline in 30 minutes, about 50% to about 65% of minocycline in 60 minutes, and about 70% to about 90% of minocycline in 120 minutes.

In another embodiment, the present application relates to a method of orally administering once daily tablet of minocycline to a subject in need thereof, comprising minocycline and one or more pharmaceutically acceptable excipient(s), comprising (i) about 20 to about 40 percent of minocycline in an immediate release (IR) portion and (ii) about 80 to about 60 percent of minocycline in an extended release (ER) portion and said tablet exhibits at least one of the following dissolution profile when measured in USP type I apparatus at 100 rpm in 900 ml of simulated gastric fluid with a pH of 2.1 and at 37° C.: about 15% to about 25% of minocycline in 15 minutes, about 35% to about 50% of minocycline in 30 minutes, about 50% to about 65% of minocycline in 60 minutes, and about 70% to about 90% of minocycline in 120 minutes.

In an embodiment, the present application relates to a method of orally administering once daily tablet of minocycline to a subject in need thereof, comprising minocycline and one or more pharmaceutically acceptable excipient(s), comprising (i) an immediate release (IR) portion and (ii) an extended release (ER) portion and said tablet exhibits at least one of the following dissolution profile when measured in USP type I apparatus at 100 rpm in 900 ml of acetate buffer with a pH of 4.5 and at 37° C.: about 15% to about 25% of minocycline in 15 minutes, about 35% to about 45% of minocycline in 30 minutes, about 50% to about 65% of minocycline in 60 minutes, and about 70% to about 90% of minocycline in 120 minutes.

In another embodiment, the present application relates to a method of orally administering once daily tablet of minocycline to a subject in need thereof, comprising minocycline and one or more pharmaceutically acceptable excipient(s), comprising (i) about 20 to about 40 percent of minocycline in an immediate release (IR) portion and (ii) about 80 to about 60 percent of minocycline in an extended release (ER) portion and said tablet exhibits at least one of the following dissolution profile when measured in USP type I apparatus at 100 rpm in 900 ml of acetate buffer with a pH of 4.5 and at 37° C.: about 15% to about 25% of minocycline in 15 minutes, about 35% to about 45% of minocycline in 30 minutes, about 50% to about 65% of minocycline in 60 minutes, and about 70% to about 90% of minocycline in 120 minutes.

In an embodiment, the present application relates to a method of orally administering once daily tablet of minocycline to a subject in need thereof, comprising minocycline and one or more pharmaceutically acceptable excipient(s), comprising (i) an immediate release (IR) portion and (ii) an extended release (ER) portion and said tablet exhibits at least one of the following dissolution profile when measured in USP type I apparatus at 100 rpm in 900 ml of phosphate buffer with a pH of 5.5 and at 37° C.: about 15% to about 25% of minocycline in 15 minutes, about 35% to about 45% of minocycline in 30 minutes, about 50% to about 65% of minocycline in 60 minutes, and about 70% to about 90% of minocycline in 120 minutes.

In another embodiment, the present application relates to a method of orally administering once daily tablet of minocycline to a subject in need thereof, comprising minocycline and one or more pharmaceutically acceptable excipient(s), comprising (i) about 20 to about 40 percent of minocycline in an immediate release (IR) portion and (ii) about 80 to about 60 percent of minocycline in an extended release (ER) portion and said tablet exhibits at least one of the following dissolution profile when measured in USP type I apparatus at 100 rpm in 900 ml of phosphate buffer with a pH of 5.5 and at 37° C.: about 15% to about 25% of minocycline in 15 minutes, about 35% to about 45% of minocycline in 30 minutes, about 50% to about 65% of minocycline in 60 minutes, and about 70% to about 90% of minocycline in 120 minutes.

In an embodiment, the present application relates to a method of treating acne by administering a once daily oral tablet of minocycline, comprising minocycline and one or more pharmaceutically acceptable excipient(s), comprising (i) an immediate release (IR) portion and (ii) an extended release (ER) portion and said tablet exhibits at least one of the following dissolution profile when measured in USP type I apparatus at 100 rpm in 900 ml of simulated gastric fluid with a pH of 2.1 and at 37° C.: about 15% to about 25% of minocycline in 15 minutes, about 35% to about 50% of minocycline in 30 minutes, about 50% to about 65% of minocycline in 60 minutes, and about 70% to about 90% of minocycline in 120 minutes.

In another embodiment, the present application relates to a method of treating acne by administering a once daily oral tablet of minocycline, comprising minocycline and one or more pharmaceutically acceptable excipient(s), comprising (i) about 20 to about 40 percent of minocycline in an immediate release (IR) portion and (ii) about 80 to about 60 percent of minocycline in an extended release (ER) portion and said tablet exhibits at least one of the following dissolution profile when measured in USP type I apparatus at 100 rpm in 900 ml of simulated gastric fluid with a pH of 2.1 and at 37° C.: about 15% to about 25% of minocycline in 15 minutes, about 35% to about 50% of minocycline in 30 minutes, about 50% to about 65% of minocycline in 60 minutes, and about 70% to about 90% of minocycline in 120 minutes.

In an embodiment, the present application relates to a method of treating acne by administering a once daily oral tablet of minocycline, comprising minocycline and one or more pharmaceutically acceptable excipient(s), comprising (i) an immediate release (IR) portion and (ii) an extended release (ER) portion and said tablet exhibits at least one of the following dissolution profile when measured in USP type I apparatus at 100 rpm in 900 ml of acetate buffer with a pH of 4.5 and at 37° C.: about 15% to about 25% of minocycline in 15 minutes, about 35% to about 45% of minocycline in 30 minutes, about 50% to about 65% of minocycline in 60 minutes, and about 70% to about 90% of minocycline in 120 minutes.

In another embodiment, the present application relates to a method of treating acne by administering a once daily oral tablet of minocycline, comprising minocycline and one or more pharmaceutically acceptable excipient(s), comprising (i) about 20 to about 40 percent of minocycline in an immediate release (IR) portion and (ii) about 80 to about 60 percent of minocycline in an extended release (ER) portion and said tablet exhibits at least one of the following dissolution profile when measured in USP type I apparatus at 100 rpm in 900 ml of acetate buffer with a pH of 4.5 and at 37° C.: about 15% to about 25% of minocycline in 15 minutes, about 35% to about 45% of minocycline in 30 minutes, about 50% to about 65% of minocycline in 60 minutes, and about 70% to about 90% of minocycline in 120 minutes.

In an embodiment, the present application relates to a method of treating acne by administering a once daily oral tablet of minocycline, comprising minocycline and one or more pharmaceutically acceptable excipient(s), comprising (i) an immediate release (IR) portion and (ii) an extended release (ER) portion and said tablet exhibits at least one of the following dissolution profile when measured in USP type I apparatus at 100 rpm in 900 ml of phosphate buffer with a pH of 5.5 and at 37° C.: about 15% to about 25% of minocycline in 15 minutes, about 35% to about 45% of minocycline in 30 minutes, about 50% to about 65% of minocycline in 60 minutes, and about 70% to about 90% of minocycline in 120 minutes.

In another embodiment, the present application relates to a method of treating acne by administering a once daily oral tablet of minocycline, comprising minocycline and one or more pharmaceutically acceptable excipient(s), comprising (i) about 20 to about 40 percent of minocycline in an immediate release (IR) portion and (ii) about 80 to about 60 percent of minocycline in an extended release (ER) portion and said tablet exhibits at least one of the following dissolution profile when measured in USP type I apparatus at 100 rpm in 900 ml of phosphate buffer with a pH of 5.5 and at 37° C.: about 15% to about 25% of minocycline in 15 minutes, about 35% to about 45% of minocycline in 30 minutes, about 50% to about 65% of minocycline in 60 minutes, and about 70% to about 90% of minocycline in 120 minutes.

In an embodiment, the present application relates to a method of orally administering once daily tablet of minocycline to a subject in need thereof, comprising minocycline and one or more cushioning agent(s) said tablet is optionally administered to a subject having lactose intolerance.

In an embodiment, the present application relates to a method of orally administering once daily tablet of minocycline to a subject in need thereof, comprising minocycline and one or more cushioning agent(s) and said tablet is optionally administered to a subject by dispersing in food dispersion or water.

In an aspect of the above embodiment, the subject is having dysphagia disorder or related swallowing difficulties.

In yet another embodiment, the present application relates to a method of orally administering once daily tablet of minocycline to a subject in need thereof, comprising minocycline and one or more cushioning agent(s) and said tablet is administered to a subject having dysphagia disorder.

In an aspect of the above embodiment, the present tablet of minocycline exhibits disintegration time from about 5 minutes to about 20 minutes in food dispersion.

In an aspect of the above embodiment, the present tablet of minocycline exhibits disintegration time of about 5, 10, 11, 12, 13, 14, 15, 16, 17, 18, 19 or 20 minutes in food dispersion.

In an aspect of the above embodiment, the present tablet of minocycline exhibits disintegration time from about 20 seconds to about 60 seconds in water.

In an aspect of the above embodiment, the present tablet of minocycline exhibits disintegration time of about 20, 25, 30, 32, 34, 36, 38, 40, 42, 44, 46, 48, 50 or 60 seconds in water.

In another embodiment, the present application relates to a method of orally administering once daily tablet of minocycline to a subject in need thereof, comprising minocycline and one or more cushioning agent(s) and said tablet is administered to a subject by dispersing in food dispersion.

In an aspect of the above embodiments, the present tablet of minocycline is stable in food dispersion for at least 1 hour.

In an embodiment, the present application relates to a once daily oral tablet of minocycline comprises of 90 mg, 105 mg, 115 mg, 135 mg or 165 mg of minocycline and one or more pharmaceutically acceptable excipient(s).

In another embodiment, the present application relates to a method of treating acne in a subject comprising orally administering once daily tablet of minocycline.

In an embodiment, the present application relates to a method of treating acne in a subject comprising orally administering once daily tablet comprising 90 mg, 105 mg, 115 mg, 135 mg or 165 mg of minocycline.

In another embodiment, the present application relates to a once daily oral tablet of minocycline comprising 90 mg, 105 mg, 115 mg, 135 mg or 165 mg of minocycline, wherein said tablet comprises (i) an immediate release (IR) portion; (ii) an extended release (ER) portion; and (iii) one or more pharmaceutically acceptable excipients.

In embodiment, the present application relates to a once daily oral tablet of minocycline comprising 90 mg, 105 mg, 115 mg, 135 mg or 165 mg of minocycline, wherein said tablet comprises (i) about 20 to about 40 percent of minocycline in an immediate release (IR) portion and (ii) about 80 to about 60 percent of minocycline in an extended release (ER) portion, and (iii) one or more pharmaceutically acceptable excipients.

In an aspect of the above embodiments, the immediate release (IR) portion comprises about 18 mg to about 66 mg of minocycline.

In an aspect of the above embodiments, the extended release (ER) portion comprises about 54 mg to about 132 mg of minocycline.

In embodiment, the present application relates to a once daily oral tablet of minocycline comprising 90 mg minocycline, wherein said tablet comprises (i) about 20 to about 40 percent of minocycline in an immediate release (IR) portion and (ii) about 80 to about 60 percent of minocycline in an extended release (ER) portion, and (iii) one or more pharmaceutically acceptable excipients.

In another embodiment, the present application relates to a once daily oral tablet of minocycline comprising 90 mg minocycline, wherein said tablet comprises (i) about 18 mg to about 36 mg minocycline in an immediate release (IR) portion; (ii) about 72 mg to about 54 mg minocycline in an extended release (ER) portion; and (iii) one or more pharmaceutically acceptable excipients.

In embodiment, the present application relates to a once daily oral tablet of minocycline comprising 105 mg minocycline, wherein said tablet comprises (i) about 20 to about 40 percent of minocycline in an immediate release (IR) portion and (ii) about 80 to about 60 percent of minocycline in an extended release (ER) portion, and (iii) one or more pharmaceutically acceptable excipients.

In another embodiment, the present application relates to a once daily oral tablet of minocycline comprising 105 mg minocycline, wherein said tablet comprises (i) about 21 mg to about 42 mg minocycline in an immediate release (IR) portion; (ii) about 84 mg to about 63 mg minocycline in an extended release (ER) portion; and (iii) one or more pharmaceutically acceptable excipients.

In embodiment, the present application relates to a once daily oral tablet of minocycline comprising 135 mg minocycline, wherein said tablet comprises (i) about 20 to about 40 percent of minocycline in an immediate release (IR) portion and (ii) about 80 to about 60 percent of minocycline in an extended release (ER) portion, and (iii) one or more pharmaceutically acceptable excipients.

In another embodiment, the present application relates to a once daily oral tablet of minocycline comprising 135 mg minocycline, wherein said tablet comprises (i) about 27 mg to about 54 mg minocycline in an immediate release (IR) portion; (ii) about 108 mg to about 81 mg minocycline in an extended release (ER) portion; and (iii) one or more pharmaceutically acceptable excipients.

In embodiment, the present application relates to a once daily oral tablet of minocycline comprising 115 mg minocycline, wherein said tablet comprises (i) about 20 to about 40 percent of minocycline in an immediate release (IR) portion and (ii) about 80 to about 60 percent of minocycline in an extended release (ER) portion, and (iii) one or more pharmaceutically acceptable excipients.

In another embodiment, the present application relates to a once daily oral tablet of minocycline comprising 115 mg minocycline, wherein said tablet comprises (i) about 23 mg to about 46 mg minocycline in an immediate release (IR) portion; (ii) about 92 mg to about 69 mg minocycline in an extended release (ER) portion; and (iii) one or more pharmaceutically acceptable excipients.

In embodiment, the present application relates to a once daily oral tablet of minocycline comprising 165 mg minocycline, wherein said tablet comprises (i) about 20 to about 40 percent of minocycline in an immediate release (IR) portion and (ii) about 80 to about 60 percent of minocycline in an extended release (ER) portion, and (iii) one or more pharmaceutically acceptable excipients.

In another embodiment, the present application relates to a once daily oral tablet of minocycline comprising 165 mg minocycline, wherein said tablet comprises (i) about 33 mg to about 66 mg minocycline in an immediate release (IR) portion; (ii) about 132 mg to about 99 mg minocycline in an extended release (ER) portion; and (iii) one or more pharmaceutically acceptable excipients.

In an embodiment, the present application relates to a method of orally administering once daily tablet of minocycline comprising 90 mg, 105 mg, 115 mg, 135 mg, or 165 mg of minocycline, wherein said tablet comprises (i) about 18 mg to about 66 mg minocycline in an immediate release (IR) portion; (ii) about 54 mg to about 132 mg minocycline in an extended release (ER) portion; and (iii) one or more pharmaceutically acceptable excipients.

In an embodiment, the present application relates to a to a method of treating acne in a subject comprising orally administering once daily tablet of minocycline, comprising 90 mg, 105 mg, 115 mg, 135 mg, or 165 mg of minocycline, wherein said tablet comprises (i) about 18 mg to about 66 mg minocycline in an immediate release (IR) portion; (ii) about 54 mg to about 132 mg minocycline in an extended release (ER) portion; and (iii) one or more pharmaceutically acceptable excipients.

In another embodiment, the present application relates to a method of orally administering once daily tablet of minocycline comprising 90 mg, 105 mg, 115 mg, 135 mg, or 165 mg of minocycline, wherein said tablet comprises (i) about 20 to about 40 percent of minocycline in an immediate release (IR) portion; (ii) about 80 to about 60 percent of minocycline in an extended release (ER) portion; and (iii) one or more pharmaceutically acceptable excipients.

In yet another embodiment, the present application relates to a method of treating acne in a subject comprising orally administering once daily tablet of minocycline, wherein said tablet comprises (i) about 20 to about 40 percent of minocycline in an immediate release (IR) portion; (ii) about 80 to about 60 percent of minocycline in an extended release (ER) portion; and (iii) one or more pharmaceutically acceptable excipients.

In yet another embodiment, the present application relates to a method of treating acne in a subject comprising orally administering once daily tablet of minocycline, comprising 165 mg, 135 mg, 105 mg or 90 mg of minocycline, wherein said tablet comprises (i) about 20 to about 40 percent of minocycline in an immediate release (IR) portion; (ii) about 80 to about 60 percent of minocycline in an extended release (ER) portion; and (iii) one or more pharmaceutically acceptable excipients.

In an aspect of the above embodiments, the immediate release (IR) and extended release (ER) portions are present in a ratio of about 20:80 to about 40:60. In an aspect of the above embodiments, a once daily tablet of minocycline of the present application comprises one or more cushioning agent(s) selected from, but are not limited to, microcrystalline cellulose, silicified microcrystalline cellulose, calcium phosphate, mannitol, sorbitol, polyethylene glycol, sodium stearyl fumarate, magnesium stearate, starch, talc and the like or mixtures thereof.

The amount of one or more cushioning agents that may be used in the present application ranges from about 40% to about 60% by weight of the present tablets.

In yet another aspect of the above embodiments, a once daily tablet of minocycline of the present application comprises immediate release (IR) and extended release (ER) portions, and one or more cushioning agent(s), wherein said release portions are present with said cushioning agent(s) in a ratio of from about 40:60 to about 50:50.

In an aspect of the above embodiments, the tablet of the present application comprising minocycline has at least one score or other means of separation mark(s) for dividing the tablet into two or more equal subunits to provide a predictable and accurate fractional dose of minocycline, wherein said divided subunits have uniformity of drug content.

In an aspect of the above embodiments, the tablet of the present application comprising minocycline is administered as intact or by dividing into two or more equal subunits to provide a predictable and accurate fractional dose of minocycline.

In an aspect of the above embodiments, the tablet of the present application comprising minocycline has at least one score or other means of separation mark(s) for dividing the tablet into two or more equal subunits to provide a predictable and accurate fractional dose of minocycline, wherein said divided subunits have uniformity of drug content and provide minocycline dose of about 1 mg/kg body weight.

In an aspect of the above embodiments, the tablet of the present application comprising minocycline has at least one score or other means of separation mark(s) for dividing the tablet into two or more equal subunits to provide a predictable and accurate fractional dose of minocycline, wherein said divided subunits have uniformity of drug content and provide minocycline dose of about 0.5-1.5 mg/kg/day or about 0.7-1.3 mg/kg/day or about 1 mg/kg/day.

In yet another embodiment, the present application relates to a once daily oral tablet of minocycline comprising 90 mg minocycline, wherein said tablet comprises (i) about 18 mg to about 36 mg minocycline in an immediate release (IR) portion; (ii) about 72 mg to about 54 mg minocycline in an extended release (ER) portion; and (iii) one or more pharmaceutically acceptable excipients, wherein said tablet comprises at least one score or other means of separation mark(s) for dividing the tablet into two equal subunits to provide a predictable and accurate fractional dose.

In another embodiment, the present application relates to a once daily oral tablet of minocycline comprising 105 mg minocycline, wherein said tablet comprises (i) about 21 mg to about 42 mg minocycline in an immediate release (IR) portion; (ii) about 84 mg to about 63 mg minocycline in an extended release (ER) portion; and (iii) one or more pharmaceutically acceptable excipients, wherein said tablet comprises at least one score or other means of separation mark(s) for dividing the tablet into two equal subunits to provide a predictable and accurate fractional dose.

In another embodiment, the present application relates to a once daily oral tablet of minocycline comprising 115 mg minocycline, wherein said tablet comprises (i) about 23 mg to about 46 mg minocycline in an immediate release (IR) portion; (ii) about 92 mg to about 66 mg minocycline in an extended release (ER) portion; and (iii) one or more pharmaceutically acceptable excipients, wherein said tablet comprises at least one score or other means of separation mark(s) for dividing the tablet into two equal subunits to provide a predictable and accurate fractional dose.

In another embodiment, the present application relates to a once daily oral tablet of minocycline comprising 135 mg minocycline, wherein said tablet comprises (i) about 27 mg to about 54 mg minocycline in an immediate release (IR) portion; (ii) about 108 mg to about 81 mg minocycline in an extended release (ER) portion; and (iii) one or more pharmaceutically acceptable excipients, wherein said tablet comprises at least one score or other means of separation mark(s) for dividing the tablet into two equal subunits to provide a predictable and accurate fractional dose.

In another embodiment, the present application relates to a once daily oral tablet of minocycline comprising 165 mg minocycline, wherein said tablet comprises (i) about 33 mg to about 66 mg minocycline in an immediate release (IR) portion; (ii) about 132 mg to about 99 mg minocycline in an extended release (ER) portion; and (iii) one or more pharmaceutically acceptable excipients, wherein said tablet comprises at least one score or other means of separation mark(s) for dividing the tablet into equal subunits to provide a predictable and accurate fractional dose.

In yet another embodiment, the present application relates to a method of orally administering once daily tablet of minocycline comprising 90 mg, 105 mg, 115 mg, 135 mg, or 165 mg of minocycline, wherein said tablet comprises (i) about 18 mg to about 66 mg minocycline in an immediate release (IR) portion; (ii) about 54 mg to about 132 mg minocycline in an extended release (ER) portion; and (iii) one or more pharmaceutically acceptable excipients, wherein said tablet comprises at least one score or other means of separation mark(s) for dividing the tablet into two equal subunits to provide a predictable and accurate fractional dose.

In yet another embodiment, the present application relates to a method of treating acne in a subject comprising orally administering once daily tablet of minocycline, comprising 90 mg, 105 mg, 115 mg, 135 mg or 165 mg of minocycline, wherein said tablet comprises (i) about 18 mg to about 66 mg minocycline in an immediate release (IR) portion; (ii) about 54 mg to about 132 mg minocycline in an extended release (ER) portion; and (iii) one or more pharmaceutically acceptable excipients, wherein said tablet comprises at least one score or other means of separation mark(s) for dividing the tablet into two equal subunits to provide a predictable and accurate fractional dose.

In an embodiment, the present application relates to a method of orally administering once daily tablet of minocycline to a subject in need thereof, comprising 90 mg, 105 mg, 115 mg, 135 mg or 165 mg of minocycline, wherein said tablet is administered as intact or by dividing into two or more equal subunits to provide minocycline dose of about 1 mg/kg body weight.

In another embodiment, the present application relates to a method of treating acne in a subject comprising orally administering once daily tablet of minocycline, comprising 90 mg, 105 mg, 115 mg, 135 mg or 165 mg of minocycline, wherein said tablet is administered as intact or by dividing into two or more equal subunits to provide minocycline dose of about 1 mg/kg body weight.

In an embodiment, the present application relates to a once daily oral tablet of minocycline comprising 90 mg, 105 mg, 115 mg, 135 mg or 165 mg of minocycline and one or more pharmaceutically acceptable excipient(s), wherein said tablet comprises (i) an immediate release (IR) portion; (ii) an extended release (ER) portion; and (iii) one or more pharmaceutically acceptable excipients and provides minocycline dose of about 1 mg/kg body weight.

In another embodiment, the present application relates to a method of orally administering once daily tablet of minocycline comprising 90 mg, 105 mg, 115 mg, 135 mg or 165 mg of minocycline and one or more pharmaceutically acceptable excipient(s), wherein said tablet comprises (i) an immediate release (IR) portion; (ii) an extended release (ER) portion; and (iii) one or more pharmaceutically acceptable excipients and provides minocycline dose of about 1 mg/kg body weight.

In yet another embodiment, the present application relates to a method of treating acne in a subject comprising orally administering once daily tablet of minocycline, comprising 90 mg, 105 mg, 115 mg, 135 mg or 165 mg of minocycline and one or more pharmaceutically acceptable excipient(s), wherein said tablet comprises (i) an immediate release (IR) portion; (ii) an extended release (ER) portion; and (iii) one or more pharmaceutically acceptable excipients and provides minocycline dose of about 1 mg/kg body weight.

In an aspect of the above embodiments, the tablet of the present application comprising minocycline has homogeneity of the amount of minocycline as intact tablet and even after dividing into equal subunits, wherein the content uniformity is about 90.0% to 105.0% of the label claim and the relative standard deviation is less than 2.0%, when measured by content uniformity test as per United States Pharmacopoeia (USP).

In an aspect of the above embodiments, the once daily tablet comprising 90 mg, 105 mg, 115 mg, 135 mg or 165 mg of minocycline of the present application provides minocycline dose of approximately about 0.5-1.5 mg/kg/day or about 0.7-1.3 mg/kg/day or about 1 mg/kg/day, wherein said tablet is dispensed to a subject for treating acne, as intact or by dividing into equal subunits according to the body weight of said subjects, as mentioned below:

| Subject's body weight (kg) | Tablet strength (mg) | mg/kg/day dose |
| --- | --- | --- |
| 35-39 | 35 | 1.0-0.89 |
| 40-49 | 45 | 1.12-0.91 |
| 45-49 | 52.5 | 1.17-1.07 |

| Subject's body weight (kg) | Tablet strength (mg) | mg/kg/day dose |
| --- | --- | --- |
| 50-59 | 52.5 | 1.05-0.89 |
| 50-59 | 55 | 1.1-0.93 |
| 60-71 | 67.5 | 1.13-0.95 |
| 72-84 | 67.5 | 0.94-0.80 |
| 60-80 | 70 | 1.16-0.87 |
| 80-88 | 82.5 | 0.96-1.06 |
| 81-96 | 90 | 1.11-0.93 |
| 85-96 | 105 | 1.24-1.09 |
| 97-110 | 105 | 1.08-0.95 |
| 110-120 | 110 | 1.0-0.91 |
| 111-125 | 135 | 1.22-1.08 |
| 126-136 | 135 | 1.07-0.99 |
| 146-165 | 165 | 1.13-1.0 |

In an aspect of the above embodiments, the tablet of the present application comprising 90 mg of minocycline upon dividing into two equal subunits provides 45 mg strengths of minocycline.

In an aspect of the above embodiments, the tablet of the present application comprising 90 mg of minocycline dispenses as intact to subjects having body weight of 81-96 mg.

In an aspect of the above embodiments, the tablet of the present application comprising 90 mg of minocycline, wherein said tablet upon dividing into two equal subunits provides 45 mg strengths of minocycline and dispensed to subjects having body weight of 40-49 kg.

In an aspect of the above embodiments, the tablet of the present application comprising 105 mg of minocycline provides 35 mg, 52.5 mg or 105 mg strengths of minocycline.

In an aspect of the above embodiments, the tablet of the present application comprising 105 mg of minocycline upon dividing into two equal subunits provides 52.5 mg strengths of minocycline.

In an aspect of the above embodiments, the tablet of the present application comprising 105 mg of minocycline upon dividing into three equal subunits provides 35 mg strengths of minocycline.

In an aspect of the above embodiments, the tablet of the present application comprising 105 mg of minocycline dispensed as intact to subjects having body weight of 85-110 kg.

In an aspect of the above embodiments, the tablet of the present application comprising 105 mg of minocycline, wherein said tablet upon dividing into two equal subunits provides 52.5 mg strengths of minocycline and dispensed to subjects having body weight of 45-59 kg.

In an aspect of the above embodiments, the tablet of the present application comprising 115 mg of minocycline, wherein said tablet upon dividing into two equal subunits provides 57.5 mg strengths of minocycline.

In an aspect of the above embodiments, the tablet of the present application comprising 115 mg of minocycline provides 57.5 mg or 115 mg strengths of minocycline.

In an aspect of the above embodiments, the tablet of the present application comprising 105 mg of minocycline, wherein said tablet upon dividing into three equal subunits provides 35 mg strengths of minocycline and dispensed to subjects having body weight of 35-39 kg.

In an aspect of the above embodiments, the tablet of the present application comprising 135 mg of minocycline provides 45 mg, 67.5 mg or 135 mg strengths of minocycline.

In an aspect of the above embodiments, the tablet of the present application comprising 135 mg of minocycline upon dividing into two equal subunits provides 67.5 mg strengths of minocycline.

In an aspect of the above embodiments, the tablet of the present application comprising 135 mg of minocycline upon dividing into three equal subunits provides 45 mg strengths of minocycline.

In an aspect of the above embodiments, the tablet of the present application comprising 135 mg of minocycline dispensed as intact to subjects having body weight of 111-136 kg.

In an aspect of the above embodiments, the tablet of the present application comprising 135 mg of minocycline, wherein said tablet upon dividing into two equal subunits provides 67.5 mg strengths of minocycline and dispensed to subjects having body weight of 60-84 kg.

In an aspect of the above embodiments, the tablet of the present application comprising 135 mg of minocycline, wherein said tablet upon dividing into three equal subunits provides 45 mg strengths of minocycline and dispensed to subjects having body weight of 40-49 kg.

In an aspect of the above embodiments, the tablet of the present application comprising 165 mg of minocycline provides 55 mg, 82.5 mg or 165 mg strengths of minocycline.

In an aspect of the above embodiments, the tablet of the present application comprising 165 mg of minocycline upon dividing into two equal subunits provides 82.5 mg strengths of minocycline.

In an aspect of the above embodiments, the tablet of the present application comprising 165 mg of minocycline upon dividing into three equal subunits provides 55 mg strengths of minocycline.

In an aspect of the above embodiments, the tablet of the present application comprising 165 mg of minocycline dispensed as intact to subjects having body weight of 146-165 kg.

In an aspect of the above embodiments, the tablet of the present application comprising 165 mg of minocycline, wherein said tablet upon dividing into two equal subunits provides 82.5 mg strengths of minocycline and dispensed to subjects having body weight of 80-88 kg.

In an aspect of the above embodiments, the tablet of the present application comprising 165 mg of minocycline, wherein said tablet upon dividing into three equal subunits provides 55 mg strengths of minocycline and dispensed to subjects having body weight of 50-59 kg.

In an aspect of the above embodiments, the tablet of the present application comprising 90 mg of minocycline dispensed, (i) as intact to subjects having body weight of 81-96 kg or (ii) by dividing into two equal subunits, wherein each subunit provides 45 mg strengths of minocycline and dispensed to subjects having body weight of 40-49 kg.

In an aspect of the above embodiments, the tablet of the present application comprising 105 mg of minocycline dispensed, (i) as intact to subjects having body weight of 85-110 kg or (ii) by dividing into two equal subunits, wherein each subunit provides 52.5 mg strengths of minocycline and dispensed to subjects having body weight of 45-59 kg or (iii) by dividing into three subunits, wherein each subunit provides 35 mg strengths of minocycline and dispensed to subjects having body weight of 35-39 kg.

In an aspect of the above embodiments, the tablet of the present application comprising 135 mg of minocycline dispensed, (i) as intact to subjects having body weight of 111-136 kg or (ii) by diving into two equal subunits, wherein each subunit provides 67.5 mg strengths of minocycline and dispensed to subjects having body weight of 60-84 kg or (iii) by diving into three subunits, wherein each subunit provides 45 mg strengths of minocycline and dispensed to subjects having body weight of 40-49 kg.

In an aspect of the above embodiments, the tablet of the present application comprising 165 mg of minocycline dispensed, (i) as intact to subjects having body weight of 146-165 kg or (ii) by dividing into two equal subunits, wherein each subunit provides 82.5 mg strengths of minocycline and dispensed to subjects having body weight of 80-88 kg or (iii) by dividing into three equal subunits, wherein each subunit provides 55 mg strengths of minocycline and dispensed to subjects having body weight of 50-59 kg.

In an aspect of the above embodiments, the tablet of the present application is administered to a subject for treating acne.

In an aspect of the above embodiments, the tablet of the present application comprising minocycline is administered as intact or upon dividing into two or more equal subunits, wherein said each subunits and an intact tablet exhibit the similar dissolution profiles when measured in USP type I apparatus at 100 rpm in 900 ml of simulated gastric fluid with a pH of 2.1 and at 37° C.

In an aspect of the above embodiments, the tablet of the present application comprising minocycline is administered as intact or upon dividing into two or more equal subunits, wherein said each subunits and an intact tablet exhibit at least one of the following dissolution profile when measured in USP type I apparatus at 100 rpm in 900 ml of simulated gastric fluid with a pH of 2.1 and at 37° C.: about 15% to about 25% of minocycline in 15 minutes, about 35% to about 50% of minocycline in 30 minutes, about 50% to about 65% of minocycline in 60 minutes, and about 70% to about 90% of minocycline in 120 minutes.

In an aspect of the above embodiments, the tablet of the present application comprising minocycline is administered as intact or upon dividing into two or more equal subunits, wherein said each subunits and an intact tablet exhibit the similar dissolution profiles when measured in USP type I apparatus at 100 rpm in 900 ml of acetate buffer with a pH of 4.5 and at 37° C.

In an aspect of the above embodiments, the tablet of the present application comprising minocycline is administered as intact or upon dividing into two or more equal subunits, wherein said each subunits and an intact tablet exhibit at least one of the following dissolution profiles when measured in USP type I apparatus at 100 rpm in 900 ml of acetate buffer with a pH of 4.5 and at 37° C.: about 15% to about 25% of minocycline in 15 minutes, about 35% to about 45% of minocycline in 30 minutes, about 50% to about 65% of minocycline in 60 minutes, and about 70% to about 90% of minocycline in 120 minutes.

In an aspect of the above embodiments, the tablet of the present application comprising minocycline is administered as intact or upon dividing into two or more equal subunits, wherein said each subunits and an intact tablet exhibit the similar dissolution profiles when measured in USP type I apparatus at 100 rpm in 900 ml of phosphate buffer with a pH of 5.5 and at 37° C.

In an aspect of the above embodiments, the tablet of the present application comprising minocycline is administered as intact or upon dividing into two or more equal subunits, wherein said each subunits and an intact tablet exhibit at least one of the following dissolution profiles when measured in USP type I apparatus at 100 rpm in 900 ml of phosphate buffer with a pH of 5.5 and at 37° C.: about 15% to about 25% of minocycline in 15 minutes, about 35% to about 45% of minocycline in 30 minutes, about 50% to about 65% of minocycline in 60 minutes, and about 70% to about 90% of minocycline in 120 minutes.

In an embodiment, the present application relates to a composition of minocycline, comprising minocycline and one or more pharmaceutically acceptable excipient(s), comprising (i) an immediate release (IR) portion and (ii) an extended release (ER) portion and said tablet when administered to healthy human subjects, provides $T_{max}$ of about 1.5 hours to about 3.75 hours.

In an embodiment, the present application relates to a composition of minocycline, comprising minocycline and one or more pharmaceutically acceptable excipient(s), comprising (i) an immediate release (IR) portion and (ii) an extended release (ER) portion and said tablet when administered to healthy human subjects in fasting condition, provides $T_{max}$ of about 1.5 hours to about 2.5 hours.

In another embodiment, the present application relates to a composition of minocycline, comprising minocycline and one or more pharmaceutically acceptable excipient(s), comprising (i) an immediate release (IR) portion and (ii) an extended release (ER) portion and said tablet when administered to healthy human subjects in fed condition, provides $T_{max}$ of about 2.5 hours to about 4.5 hours.

In another embodiment, the composition of the present application is provided in various minocycline strengths such as about 10 mg to about 165 mg, specifically about 10 mg to about 135 mg.

In another embodiment, various minocycline strengths of the present application include, but not limited to, 10 mg, 15 mg, 20 mg, 25 mg, 30 mg, 35 mg, 40 mg, 45 mg, 52.5 mg, 55 mg, 67.5 mg, 70 mg, 82.5 mg, 90 mg, 1.5 mg, 110 mg, 115 mg, 135 mg and 165 mg.

In an embodiment, the present application relates to a once daily oral tablet of minocycline, comprising minocycline and one or more pharmaceutically acceptable excipient(s), comprising (i) an immediate release (IR) portion and (ii) an extended release (ER) portion and said tablet when administered to healthy human subjects, provides $T_{max}$ of about 1.5 hours to about 3.75 hours.

In an embodiment, the present application relates to a once daily oral tablet of minocycline, comprising minocycline and one or more pharmaceutically acceptable excipient(s), comprising (i) an immediate release (IR) portion and (ii) an extended release (ER) portion and said tablet when administered to healthy human subjects in fasting condition, provides $T_{max}$ of about 1.5 hours to about 2.5 hours.

In another embodiment, the present application relates to a once daily oral tablet of minocycline, comprising minocycline and one or more pharmaceutically acceptable excipient(s), comprising (i) an immediate release (IR) portion and (ii) an extended release (ER) portion and said tablet when administered to healthy human subjects in fed condition, provides $T_{max}$ of about 2.5 hours to about 4.5 hours.

In another embodiment, the present application relates to a once daily oral tablet of minocycline, comprising minocycline and one or more pharmaceutically acceptable excipient(s), comprising (i) about 20 to about 40 percent of minocycline in an immediate release (IR) portion and (ii) about 80 to about 60 percent of minocycline in an extended release (ER) portion and said tablet when administered to healthy human subjects in fasting condition, provides $T_{max}$ of about 1.5 hours to about 2.5 hours.

In another embodiment, the present application relates to a once daily oral tablet of minocycline, comprising minocycline and one or more pharmaceutically acceptable excipient(s), comprising (i) about 20 to about 40 percent of minocycline in an immediate release (IR) portion and (ii) about 80 to about 60 percent of minocycline in an extended release (ER) portion and said tablet when administered to healthy human subjects in fed condition, provides $T_{max}$ of about 2.5 hours to about 4.5 hours.

In an embodiment, the present application relates to a once daily oral tablet of minocycline, comprising 135 mg of minocycline and one or more pharmaceutically acceptable excipient(s), comprising (i) an immediate release (IR) portion and (ii) an extended release (ER) portion and said tablet when administered to healthy human subjects in fasting and fed conditions, provides at least one of the following pharmacokinetic parameters: (a) a $C_{max}$ of about 400.00 ng/ml to about 1000.00 ng/ml, (b) an $AUC_{(0-t)}$ of about 7000.00 ng·hr/ml to about 15500.00 ng·hr/ml, and (c) an $AUC_{(0-\infty)}$ ranging from about 7500.00 ng·hr/ml to about 16500.00 ng·hr/ml.

In another embodiment, the present application relates to a once daily oral tablet of minocycline, comprising 135 mg of minocycline and one or more pharmaceutically acceptable excipient(s), comprising (i) about 20 to about 40 percent of minocycline in an immediate release (IR) portion and (ii) about 80 to about 60 percent of minocycline in an extended release (ER) portion and said tablet when administered to healthy human subjects in fasting and fed conditions, provides at least one of the following pharmacokinetic parameters: (a) a $C_{max}$ of about 400.00 ng/ml to about 1000.00 ng/ml, (b) an $AUC_{(0-t)}$ of about 7000.00 ng·hr/ml to about 15500.00 ng·hr/ml, and (c) an $AUC_{(0-\infty)}$ ranging from about 7500.00 ng·hr/ml to about 16500.00 ng·hr/ml.

In another embodiment, the present application provides a composition of minocycline, comprising minocycline strength up to 165 mg and one or more pharmaceutically acceptable excipient(s), comprising (i) an immediate release (IR) portion and (ii) an extended release (ER) portion and said composition is having dose-proportional pharmacokinetic profile.

In another embodiment, the present application provides a once daily oral tablet of minocycline, comprising other minocycline dose such as 35 mg, 45 mg, 52.5 mg, 55 mg, 57.5 mg, 67.5 mg, 70 mg, 82.5 mg, 90 mg, 105 mg, 110 mg, 115 mg, 135 mg or 165 mg and one or more pharmaceutically acceptable excipient(s), comprising (i) an immediate release (IR) portion and (ii) an extended release (ER) portion and said tablet is having dose-proportional pharmacokinetic profile.

In another embodiment, the present application provides a composition of minocycline, comprising minocycline strength up to 165 mg and one or more pharmaceutically acceptable excipient(s), comprising (i) an immediate release (IR) portion and (ii) an extended release (ER) portion and said composition is having dose-proportional $C_{max}$, $AUC_{(0-t)}$ and $AUC_{(0-\infty)}$ values.

In another embodiment, the present application provides a once daily oral tablet of minocycline, comprising other minocycline dose such as 35 mg, 45 mg, 52.5 mg, 55 mg, 57.5 mg, 67.5 mg, 70 mg, 82.5 mg, 90 mg, 105 mg, 110 mg, 115 mg, 135 mg or 165 mg and one or more pharmaceutically acceptable excipient(s), comprising (i) an immediate release (IR) portion and (ii) an extended release (ER) portion and said tablet is having dose-proportional $C_{max}$, $AUC_{(0-t)}$ and $AUC_{(0-\infty)}$ values.

In another embodiment, the present application provides a composition of minocycline, comprising minocycline strength up to 135 mg and one or more pharmaceutically acceptable excipient(s), comprising (i) an immediate release (IR) portion and (ii) an extended release (ER) portion and said composition is having dose-proportional pharmacokinetic profile.

In another embodiment, the present application provides a composition of minocycline, comprising minocycline strength up to 135 mg and one or more pharmaceutically acceptable excipient(s), comprising (i) an immediate release (IR) portion and (ii) an extended release (ER) portion and said composition is having dose-proportional $C_{max}$, $AUC_{(0-t)}$ and $AUC_{(0-\infty)}$ values.

In one embodiment, the composition of the present application is administered to subjects in fasting and/or fed conditions.

In an aspect of the above embodiments, the tablet of the present application comprising minocycline exhibits bioequivalence to a corresponding SOLODYN® tablet when administered to healthy human subjects in fasting and fed conditions.

In an embodiment, the present application relates to a once daily oral tablet of minocycline, comprising minocycline and one or more pharmaceutically acceptable excipient(s), wherein said tablet comprises (i) an immediate release (IR) portion and (ii) an extended release (ER) portion and said tablet exhibits bioequivalence to a corresponding SOLODYN® tablet when administered to healthy human subjects in fasting and fed conditions.

In an embodiment, the present application relates to a once daily oral tablet of minocycline, comprising 35 mg, 45 mg, 52.5 mg, 55 mg, 57.5 mg, 67.5 mg, 70 mg, 82.5 mg, 90 mg, 105 mg, 110 mg, 115 mg, 135 mg or 165 mg of minocycline and one or more pharmaceutically acceptable excipient(s), wherein said tablet comprises (i) an immediate release (IR) portion and (ii) an extended release (ER) portion and said tablet exhibits a bioequivalence to a corresponding SOLODYN® strength when administered to healthy human subjects.

In one aspect of the above embodiment, said tablet comprises (i) about 20 to about 40 percent of minocycline in an immediate release (IR) portion and (ii) about 80 to about 60 percent of minocycline in an extended release (ER) portion.

In another embodiment, the present application relates to a once daily oral tablet of minocycline, comprising minocycline and one or more pharmaceutically acceptable excipient(s), wherein said tablet comprises (i) about 20 to about 40 percent of minocycline in an immediate release (IR) portion and (ii) about 80 to about 60 percent of minocycline in an extended release (ER) portion and said tablet exhibits bioequivalence to a corresponding SOLODYN® tablet when administered to healthy human subjects in fasting and fed conditions.

In an aspect of the above embodiments, the tablet of the present application comprising minocycline and one or more pharmaceutically acceptable excipient(s) and said tablet exhibits bioequivalence to a corresponding SOLODYN® tablet when administered to healthy human subjects in fasting and fed conditions, and said bioequivalence is established by: (a) a 90% Confidence Interval for mean $C_{max}$, which is between 80% and 125%, (b) a 90% Confidence Interval for mean $AUC_{(0-t)}$, which is between 80% and 125% and (c) a 90% Confidence Interval for mean $AUC_{(0-\infty)}$, which is between 80% and 125%.

In an embodiment, the present application relates to a once daily oral tablet of minocycline, comprising 35 mg, 45 mg, 52.5 mg, 55 mg, 57.5 mg, 67.5 mg, 70 mg, 82.5 mg, 90 mg, 105 mg, 115 mg, 110 mg, 135 mg or 165 mg of minocycline and one or more pharmaceutically acceptable excipient(s), wherein said tablet comprises (i) an immediate release (IR) portion and (ii) an extended release (ER) portion and said tablet exhibits a bioequivalence to a corresponding SOLODYN® dose when administered to healthy human subjects, and said bioequivalence is established by: (a) a 90% Confidence Interval for mean $C_{max}$, which is between 80% and 125%, (b) a 90% Confidence Interval for mean $AUC_{(0-t)}$, which is between 80% and 125% and (c) a 90% Confidence Interval for mean $AUC_{(0-\infty)}$, which is between 80% and 125%.

In an embodiment, the present application relates to a process of preparing once daily oral tablet of minocycline comprising the steps of: (i) preparing an immediate release (IR) portion; (ii) preparing an extended release (ER) portion; (iii) combining the IR and ER portions with one or more cushioning agent(s); and (iv) compressing the mixture of (iii) into a tablet.

In another embodiment, the present application relates to a process of preparing once daily oral tablet of minocycline, comprising the steps of: (i) preparing an immediate release (IR) portion comprising about 20 to about 40 percent of minocycline; (ii) preparing an extended release (ER) portion comprising about 80 to about 60 percent of minocycline; (iii) combining the IR and ER portions with one or more one or more cushioning agent(s); and (iv) compressing the mixture of (iii) into a tablet.

In another embodiment, the present application relates to a process of preparing once daily oral tablet of minocycline, comprising the steps of: (i) preparing an immediate release (IR) portion comprising about 18 mg to about 66 mg of minocycline; (ii) preparing an extended release (ER) portion comprising about 54 mg to about 132 mg of minocycline; (iii) combining the IR and ER portions with one or more one or more cushioning agent(s); and (iv) compressing the mixture of (iii) into a tablet.

In an aspect of the above embodiments, the process involves coating or layering of minocycline over inert cores with coating or layering materials comprising minocycline solution and other suitable pharmaceutical excipients like binders, plasticizers or disintegrants over the inert cores.

The process of coating or layering includes any method known to a person skilled in the art such as, but not limited to, by spraying a suspension or dispersion of said coating material in a conventional coating pan or fluidized bed equipment (such as a Wurster or Glatt) followed by drying of cores. Alternatively, said coating materials may also be applied by powder-coating, wherein the cores are maintained in a sticky state, a mixture of coating material is added continuously or periodically so as to adhere to the sticky cores, followed by drying of coated cores when desired coating is achieved.

The "inert core" as used herein, refers to a pharmaceutically acceptable inert substrate which is routinely used in formulation art, that includes, but not limited to, powder or a multiparticulate such as a granule, a pellet, a bead, a spherule, a beadlet, a microcapsule, a millisphere, a nanocapsule, a nanosphere, a microsphere or a minitablet, which comprises at least one pharmaceutically acceptable excipient selected from the group comprising of water soluble, water insoluble, water swellable or water non swellable material such as starch, sugar, microcrystalline cellulose, vegetable gums, waxes, and the like.

The inert cores may also be prepared with the techniques known to a person skilled in the art, such as, wet granulation, dry granulation, or extrusion-spheronization and the like. The inert cores have a size of diameter in the range of about 125 to about 600 microns.

Suitable solvent(s) used in the preparation of minocycline solution are selected from, but not limited to, water, methanol, ethanol, n-propanol, isopropanol, dichloromethane, acetone, absolute alcohol and the like or mixtures thereof.

Suitable examples of binder(s) that may be used in the present application include, but are not limited to, methyl cellulose, hydroxy propyl cellulose, hydroxy propyl methyl cellulose, polyvinyl pyrrolidone, polyvinyl alcohol, propylene glycol, pre gelatinized starch, oxide such as polyethylene oxide and the like or mixtures thereof. The binders may be combination of two or more, such as hydroxy propyl cellulose and hydroxy propyl methyl cellulose. The binders used in the present application have a viscosity from about 5 centipoise to about 15 centipoise.

In an aspect of the above embodiments, the binder(s) may be combination of hydroxy propyl cellulose and hydroxy propyl methyl cellulose, present in a ratio of from about 55:45 to about 75:25.

The amount of binders that may be used in the present application ranges from about 4% to about 10% by weight of the tablet.

The "loading efficiency" as used herein, refers to the binding affinity of the drug i.e. minocycline, towards inert core during a process of layering of minocycline over the inert cores to prepare tablets, and can be expressed herein as a percentage.

In an embodiment, the present application relates to a process of preparing once daily oral tablet of minocycline, comprising the steps of: (i) preparing an immediate release (IR) portion; (ii) preparing an extended release (ER) portion; (iii) combining the IR and ER portions with one or more one or more cushioning agent(s); and (iv) compressing the mixture of (iii) into a tablet, wherein said process provides loading efficiency of minocycline for the IR and/or ER portions of at least about 95%.

In another embodiment, the present application relates to a process of preparing once daily oral tablet of minocycline, comprising the steps of: (i) preparing an immediate release (IR) portion comprising about 20 to about 40 percent of minocycline; (ii) preparing an extended release (ER) portion comprising about 80 to about 60 percent of minocycline; (iii) combining the IR and ER portions with one or more one or more cushioning agent(s); and (iv) compressing the mixture of (iii) into a tablet, wherein said process provides loading efficiency of minocycline for the IR and/or ER portions of at least about 95%.

In another embodiment, the present application relates to a process of preparing once daily oral tablet of minocycline, comprising the steps of: (i) preparing an immediate release (IR) portion comprising about 18 mg to about 66 mg of minocycline; (ii) preparing an extended release (ER) portion comprising about 54 mg to about 132 mg of minocycline; (iii) combining the IR and ER portions with one or more one or more cushioning agent(s); and (iv) compressing the mixture of (iii) into a tablet, wherein said process provides loading efficiency of minocycline for the IR and/or ER portions of at least about 95%.

In an aspect of the above embodiments, the process of coating or layering of minocycline and one or more binder(s) over the inert cores, provides loading efficiency of minocycline for the IR and/or ER portions of at least about 65%, 70%, 75%, 80%, 85%, 90% or 95%.

In an aspect of the above embodiments, suitable cushioning agents that may be used in the present application include, but are not limited to, microcrystalline cellulose, silicified microcrystalline cellulose, calcium phosphate, mannitol, sorbitol, polyethylene glycol, sodium stearyl fumarate, magnesium stearate, starch, talc and the like or mixtures thereof.

In an aspect of the above embodiments, the amount of cushioning agents that may be used in the present application ranges from about 40% to about 60% by weight of the tablet.

In another aspect of the above embodiments, the extended release (ER) portion are prepared by coating the immediate release (IR) portion with one or more release modifying polymers.

In another aspect of the above embodiments, the present application relates to a process of preparing once daily tablet of minocycline comprising extended release (ER) portion, wherein the ER coating layer has a thickness of not more than 200 μm.

Suitable examples of release modifying polymers that may be used in the present application include, but are not limited to, unsubstituted alkyl celluloses or cellulose ethers like ethyl cellulose; and substituted alkyl celluloses or cellulose ethers like hydroxy alkyl celluloses and carboxy alkyl celluloses such as hydroxy ethyl cellulose, hydroxy propyl cellulose, hydroxy propyl methyl cellulose, carboxy methyl ethyl cellulose and carboxy methyl cellulose; acrylic and methacrylic acid polymers and copolymers such as methyl methacrylate, ethoxy ethyl methacrylates, ethyl acrylate, amino alkyl methacrylate copolymer, poly(acrylic acid), poly(methacrylic acid), polyacrylamide and glycidyl methacrylate copolymers; polyalkylene oxides such as polyethylene oxide and polypropylene oxide and copolymers of ethylene oxide and propylene oxide; poly vinyl alcohols, gums, synthetic resins and the like or mixtures thereof.

In an aspect of the above embodiments, the release modifying polymers may be a combination of unsubstituted and substituted alkyl celluloses or cellulose ethers, present in a ratio of from about 65:35 to about 85:15.

In an aspect of the above embodiments, the release modifying polymers may be a combination of unsubstituted alkyl celluloses or cellulose ethers like ethyl cellulose and substituted alkyl celluloses or cellulose ethers like hydroxy propyl methyl cellulose, present in a ratio of from about 65:35 to about 85:15.

The amount of release modifying polymers that may be used in the present application ranges from about 5% to about 10% by weight of the tablet.

In yet another aspect of the above embodiments, the immediate release (IR) portion of minocycline tablets of the present application, comprising minocycline layered inert cores, may further optionally have one or more barrier coating layers over said immediate release (IR) portions. Coating of barrier layer may be done by any conventional methods known in the art.

In yet another aspect of the above embodiments, the extended release (ER) portion of minocycline tablets of the present application, comprising immediate release (IR) portions of minocycline with one or more layers of release modifying polymers, may further optionally have one or more barrier coating layers over the extended release (ER) portion. Coating of barrier layer may be done by any conventional methods known in the art.

In yet another aspect of the above embodiments, the barrier coating layer over immediate release (IR) portions or extended release (ER) portions include polymers selected from the group comprising, but not limited to, cellulose derivatives like methyl cellulose, carboxy methyl cellulose, hydroxy propyl cellulose or hydroxy propyl methyl cellulose; polyethylene glycol, starch and the like or mixtures thereof.

The amount of barrier coating polymers that may be used in the present application ranges from about 5% to about 10% by weight of the tablet.

In yet another aspect of the above embodiments, the barrier coated immediate release (IR) portion of minocycline tablets of the present application, comprising minocycline layered inert cores, may further optionally have one or more top or seal coating layers over said immediate release (IR) portions. Coating of top or seal layer may be done by any conventional methods known in the art.

In yet another aspect of the above embodiments, the barrier coated extended release (ER) portion of minocycline tablets of the present application, comprising immediate release (IR) portions of minocycline with one or more layers of release modifying polymers, may further optionally have one or more top or seal coating layers over the extended release (ER) portion. Coating of top or seal layer may be done by any conventional methods known in the art.

In yet another aspect of the above embodiments, the top or seal coating layer over barrier coated immediate release (IR) portions or extended release (ER) portions include polymers selected from the group comprising, but not limited to, cellulose derivatives like methyl cellulose, carboxy methyl cellulose, hydroxy propyl cellulose or hydroxy propyl methyl cellulose; polyethylene glycol, starch and the like or mixtures thereof.

The amount of top or seal coating polymers that may be used in the present application ranges from about 5% to about 10% by weight of the tablet.

In yet another aspect of the above embodiments, the minocycline tablets of the present application provides tablets having appropriate hardness, friability and tensile strength (force required to break the tablet) that will withstand the subsequent packaging. Also the tablets offer uniformity of drug content, such that when the tablet can be divided into equal portions, it provides a required fractional dose.

In yet another aspect of the above embodiments, the present application relates to a process of preparing tablet of minocycline, wherein said tablet has hardness of about 25 to about 40 kilopascal and friability is less than 1%.

In another embodiment, the tablet of minocycline of present application may comprises one or more pharmaceutically acceptable excipient(s) selected from lubricants, glidants, anti-tacking agents, plasticizers, disintegrants or opacifying agents and the like or mixtures thereof.

The lubricant, glidant or anti-tacking agent may be used interchangeably in the composition of the present application and are selected from, but not limited to, metallic stearates such as magnesium stearate, calcium stearate, zinc stearate; stearic acid, hydrogenated vegetable oil, hydrogenated castor oil, glyceryl palmitostearate, glyceryl behenate, polyethylene glycols, corn starch, sodium stearyl fumarate, sodium benzoate, mineral oil, talc, colloidal silicon dioxide, magnesium trisilicate, powdered cellulose, starch, tribasic calcium phosphate and the like or mixtures thereof. The amount of such agents may range from about 0.1% w/w to about 10% w/w of the tablet.

The plasticizer used in the composition of the present application may be used in the coating layer to increase the flexibility and strength of the coat/layer, and suitable plasticizer may be selected from, but not limited to, propylene glycol, polyethylene glycol, triethyl citrate, acetyl triethyl citrate, diethyl phthalate, dibutyl phthalate, dibutyl sebacate, tributyl citrate or mixtures thereof. The plasticizer may be present in amounts ranging from about 0.1% to about 20% w/w of the tablet.

The disintegrant used in the composition of the present application may be selected from, but not limited to, crospovidone, sodium starch glycolate, croscarmellose sodium, croscarmellose potassium, croscarmellose calcium, carboxymethylcellulose, pregelatinized starch, carboxymethyl starch and the like or mixtures thereof. The disintegrant may be present in amount from 1% to 20% by weight of the tablet.

In an embodiment, the present application relates to a once daily oral tablet of minocycline, wherein said tablet comprises (i) an immediate release (IR) portion, (ii) an extended release (ER) portion, and (iii) one or more cushioning agent(s), wherein said immediate release (IR) and extended release (ER) portions are present in a ratio of about 20:80 to about 40:60 and said immediate release (IR) and extended release (ER) portions are present with said cushioning agent(s) present in a ratio of from about 40:60 to about 50:50.

In another embodiment, the present application relates to a once daily oral tablet of minocycline, wherein said tablet comprises (i) about 20 to about 40 percent of minocycline in an immediate release (IR) portion (ii) about 80 to about 60 percent of minocycline in an extended release (ER) portion comprising said IR portion, and (iii) one or more cushioning agent(s), wherein said immediate release (IR) and extended release (ER) portions are present in a ratio of about 20:80 to about 40:60 and said immediate release (IR) and extended release (ER) portions are present with said cushioning agent(s) present in a ratio of from about 40:60 to about 50:50.

In another embodiment, the present application relates to a once daily oral tablet of minocycline, wherein said tablet comprises (i) about 20 to about 40 percent of minocycline in an immediate release (IR) portion (ii) about 80 to about 60 percent of minocycline in an extended release (ER) portion comprising said IR portion, and (iii) one or more cushioning agent(s), wherein said immediate release (IR) and extended release (ER) portions are present in a ratio of about 20:80 to about 40:60 and said immediate release (IR) and extended release (ER) portions are present with said cushioning agent(s) present in a ratio of from about 40:60 to about 50:50 and said tablet exhibit at least one of the following dissolution profile when measured in USP type I apparatus at 100 rpm in 900 ml of simulated gastric fluid with a pH of 2.1 and at 37° C.: about 15% to about 25% of minocycline in 15 minutes, about 35% to about 50% of minocycline in 30 minutes, about 50% to about 65% of minocycline in 60 minutes, and about 70% to about 90% of minocycline in 120 minutes.

In an aspect of the above embodiments, said immediate release (IR) portion of the present tablet comprises hydroxy propyl cellulose and hydroxy propyl methyl cellulose present in a ratio of from about 55:45 to about 75:25.

In an aspect of the above embodiments, said extended release (ER) portion of the present tablet comprises ethyl cellulose and hydroxy propyl methyl cellulose present in a ratio of from about 65:35 to about 85:15.

In an embodiment, the present application relates to a method of orally administering once daily tablet of minocycline, wherein said tablet is dispensed in a suitable tablet storage container with a storage means for storing and dispensing intact tablets and/or subunits of any divided tablets.

In another embodiment, the present application relates to a method of treating acne in a subject comprising orally administering once daily tablet of minocycline, wherein said tablet is dispensed in a suitable tablet storage container with a storage means for storing and dispensing intact tablets and/or subunits of any divided tablets.

In an aspect of above embodiment, the tablet storage container comprises any suitable packaging material known in the art that can ensure the stability of the minocycline during storage and in transit.

In one aspect, compositions defined in various embodiments of the present application are substantially free of lactose.

In another aspect, compositions applied in methods defined in several embodiments of the present application are substantially free of lactose.

In another aspect, compositions defined in various embodiments of the present application are administered to a subject for a method of treating acne.

The "stock keeping unit" or "SKU" as used herein, refers to individual dosage form package unit or container, containing single strength of drug.

The "inventory" as used herein, refers to minocycline dosage units that a firm or person holds in stock with the intent of selling, distributing, administering or transforming it into a more valuable state.

The "inventory optimization" as used herein, refers to improve inventory for SKU comprising the present tablets of minocycline, which includes various inventory optimization benefits like, but are not limited to, improved cash flow by reducing inventory maintenance and occupancy costs, reduced pharmacy time spent to manage purchasing and inventory functions, improved visibility to inventory management performance, educating buyer on the financial impact of purchasing and inventory management, decreased expired medication waste, reduced storage space occupied for said tablets of minocycline and the like, and said inventory optimization provides at least 50% reduced SKU in a pharmacy or warehouse.

The term "shared inventory" as used herein, refers to supply of the present tablets of minocycline, wherein said supply includes carrying inventory comprising multiple minocycline strengths in a single tablet packaged in a single container, which aims to reduce at least 50% total cost of supply chain and its maintenance by providing reduced Inventory lot size and storage space in a pharmacy or warehouse.

In an embodiment, the present application relates to a once daily oral tablet of minocycline comprising, 90 mg, 105 mg, 115 mg, 135 mg or 165 mg of minocycline, wherein said tablet is supplied to a pharmacy or stored in a warehouse to provide at least 50% reduced stock keeping units for said strengths of minocycline.

In another embodiment, the present application relates to a once daily oral tablet of minocycline comprising, 90 mg, 105 mg, 115 mg, 135 mg or 165 mg of minocycline, wherein said tablet provides a shared inventory by providing at least 50% reduced supply cost as well as storage, maintenance, and occupancy cost in a pharmacy or warehouse for said tablets of minocycline.

In an aspect of the above embodiments, the tablet of the present application comprising, 90 mg, 105 mg, 115 mg, 135 mg or 165 mg of minocycline provides inventory optimization to a pharmacy or a warehouse for said strengths of minocycline.

In an aspect of the above embodiments, the tablet of the present application comprising 90 mg of minocycline provides inventory optimization to a pharmacy or a warehouse by providing 45 mg or 90 mg strengths of minocycline in scored tablets.

In an aspect of the above embodiments, the tablet of the present application comprising 105 mg of minocycline provides inventory optimization to a pharmacy or a warehouse by providing 35 mg, 52.5 mg or 105 mg strengths of minocycline in scored tablets.

In an aspect of the above embodiments, the tablet of the present application comprising 115 mg of minocycline provides inventory optimization to a pharmacy or a warehouse by providing 57.5 mg or 115 mg strengths of minocycline in scored tablets.

In an aspect of the above embodiments, the tablet of the present application comprising 135 mg of minocycline provides inventory optimization to a pharmacy or a warehouse by providing 45 mg, 67.5 mg or 135 mg strengths of minocycline in scored tablets.

In an aspect of the above embodiments, the tablet of the present application comprising 165 mg of minocycline provides inventory optimization to a pharmacy or a warehouse by providing 55 mg, 82.5 mg or 165 mg strengths of minocycline in scored tablets. In an aspect of the above embodiments, the present tablet provides minocycline dose of approximately 1 mg/kg body weight.

In an aspect of the above embodiments, the present tablet is dispensed to a subject for treating acne.

In an aspect of the above embodiments, the present tablet is dispensed as intact or by dividing into two or more equal subunits.

In an embodiment, the present application relates to a once daily oral tablet of minocycline comprising 90 mg, 105 mg, 115 mg, 135 mg or 165 mg of minocycline, wherein said tablet is supplied to a pharmacy or warehouse in a suitable tablet storage container with a storage means for storing and dispensing intact tablets and/or subunits of any divided tablets.

In another embodiment, the present application relates to a once daily oral tablet of minocycline comprising 90 mg, 105 mg, 115 mg, 135 mg or 165 mg of minocycline, wherein said tablet is dispensed to a subject for treating acne in a suitable tablet storage container with a storage means for storing and dispensing intact tablets and/or subunits of any divided tablets.

In an aspect of above embodiment, the tablet storage container comprises any suitable packaging material known in the art that can ensure the stability of the minocycline during storage and in transit.

In an embodiment, the present application relates to a once daily oral tablet of minocycline comprises of 35 mg, 45 mg, 52.5 mg, 55 mg, 57.5 mg, 67.5 mg, 70 mg, 82.5 mg, 90 mg, 105 mg, 110 mg, 115 mg, 135 mg or 165 mg of minocycline and one or more pharmaceutically acceptable excipient(s).

In another embodiment, the present application relates to a method of treating acne in a patient comprising orally administering the composition of minocycline.

In an embodiment, the present application relates to a method of treating acne in a patient comprising orally administering a once daily oral tablet of minocycline comprises of 35 mg, 45 mg, 52.5 mg, 55 mg, 57.5 mg, 67.5 mg, 70 mg, 82.5 mg, 90 mg, 105 mg, 110 mg, 115 mg, 135 mg or 165 mg of minocycline.

In another embodiment, the present application relates to a composition of minocycline, comprising minocycline and one or more pharmaceutically acceptable excipient(s), comprising (i) about 20 to about 40 percent of minocycline in an immediate release (IR) portion and (ii) about 80 to about 60 percent of minocycline in an extended release (ER) portion and said tablet exhibits at least one of the following dissolution profile when measured in USP type I apparatus at 100 rpm in 900 ml of simulated gastric fluid with a pH of 2.1 and at 37° C.: about 15% to about 25% of minocycline in 15 minutes, about 35% to about 50% of minocycline in 30 minutes, about 50% to about 65% of minocycline in 60 minutes, and about 70% to about 90% of minocycline in 120 minutes.

In another embodiment, the present application relates to a composition of minocycline, comprising minocycline and one or more pharmaceutically acceptable excipient(s), comprising (i) about 20 to about 40 percent of minocycline in an immediate release (IR) portion and (ii) about 80 to about 60 percent of minocycline in an extended release (ER) portion and said tablet exhibits at least one of the following dissolution profile when measured in USP type I apparatus at 100 rpm in 900 ml of acetate buffer with a pH of 4.5 and at 37° C.: about 15% to about 25% of minocycline in 15 minutes, about 35% to about 45% of minocycline in 30 minutes, about 50% to about 65% of minocycline in 60 minutes, and about 70% to about 90% of minocycline in 120 minutes.

In another embodiment, the present application relates to a composition of minocycline, comprising minocycline and one or more pharmaceutically acceptable excipient(s), comprising (i) about 20 to about 40 percent of minocycline in an immediate release (IR) portion and (ii) about 80 to about 60 percent of minocycline in an extended release (ER) portion and said tablet exhibits at least one of the following dissolution profile when measured in USP type I apparatus at 100 rpm in 900 ml of phosphate buffer with a pH of 5.5 and at 37° C.: about 15% to about 25% of minocycline in 15 minutes, about 35% to about 45% of minocycline in 30 minutes, about 50% to about 65% of minocycline in 60 minutes, and about 70% to about 90% of minocycline in 120 minutes.

The present application is further illustrated by the examples which are provided merely to be exemplary of the pharmaceutical composition described above and do not limit the scope of the application. Certain modifications and equivalents will be apparent to those skilled in the art and are intended to be included within the scope of the present application.

The present invention is illustrated below by reference to the following examples. However, one skilled in the art will appreciate that the specific methods and results discussed are merely illustrative of the present invention, and not to be construed as limiting the application. The following examples may include compilations of data that are representative of data gathered at various times during the course of development and experimentation related to the present invention.

EXAMPLES

Examples 1-3

The tablets of the present application comprising minocycline are prepared as described herein.

TABLE 1

| Composition | Quantity per unit (%) | | | |
| --- | --- | --- | --- | --- |
| | Ex-1 | Ex-2 | Ex-3 | Ex-4 |
| Drug loading | | | | |
| Inert core | 14.86 | 13 | 12.66 | 13 |
| Minocycline Hydrochloride (equivalent to Minocycline 135 mg) | 15.8 | 12.67 | 13.46 | 12.67 |
| Hydroxy propyl cellulose | 3.45 | 3.45 | 3.45 | 3.45 |
| Hydroxy propyl methyl cellulose | 1.80 | 1.85 | 1.85 | 1.85 |
| Polyethylene glycol 400 | 0.52 | 0.69 | 0.67 | 0.69 |
| Talc | 0.79 | 1.82 | 1.77 | 1.82 |
| Water quantity sufficient to 15.7% w/w | quantity sufficient | quantity sufficient | quantity sufficient | quantity sufficient |
| Total | 37.22 | 33.53 | 33.71 | 33.53 |
| Barrier coating | | | | |
| Hydroxy propyl methyl cellulose | 1.86 | 1.67 | 1.68 | 1.67 |
| Polyethylene glycol 400 | 0.18 | 0.16 | 0.16 | 0.16 |
| Talc | 0.55 | 0.50 | 0.50 | 0.50 |
| Water | quantity sufficient | quantity sufficient | quantity sufficient | quantity sufficient |
| Total | 2.59 | 2.34 | 2.35 | 2.34 |
| Extended release coating | | | | |
| Ethyl cellulose | 5.43 | 4.69 | 3.93 | 4.69 |
| Hydroxy propyl methyl cellulose | 1.81 | 1.56 | 1.31 | 1.56 |
| Triethyl citrate | 0.54 | 0.46 | 0.39 | 0.46 |
| Talc | 2.17 | 1.87 | 1.57 | 1.87 |
| Isopropyl alcohol | quantity sufficient | quantity sufficient | quantity sufficient | quantity sufficient |
| Water | quantity sufficient | quantity sufficient | quantity sufficient | quantity sufficient |
| Total | 9.95 | 8.60 | 7.2 | 8.60 |
| Outer top coating | | | | |
| Hydroxy propyl methyl cellulose | 5.34 | 3.80 | 3.86 | 3.80 |
| Polyethylene glycol 400 | 0.53 | 0.38 | 0.38 | 0.38 |
| Talc | 1.60 | 1.13 | 1.16 | 1.13 |
| Water | quantity sufficient | quantity sufficient | quantity sufficient | quantity sufficient |
| Total | 7.47 | 5.32 | 5.4 | 5.32 |
| Top coating to barrier coating | | | | |
| Hydroxy propyl methyl cellulose | — | — | 0.77 | — |
| Polyethylene glycol 400 | — | — | 0.07 | — |
| Talc | — | — | 0.23 | — |
| Water | — | — | quantity sufficient | — |
| Total | — | — | 1.07 | — |

TABLE 1-continued

| Composition | Quantity per unit (%) | | | |
|---|---|---|---|---|
| | Ex-1 | Ex - 2 | Ex - 3 | Ex - 4 |
| Compression stage | | | | |
| Outer top coated portions + Barrier coated portions/ Top coating to barrier coated portions | 53.7 | 49.81 | 49.81 | 49.81 |
| Silicified microcrystalline cellulose | 41.24 | 44.83 | 44.83 | 44.83 |
| Microcrystalline cellulose | 4.58 | 4.98 | 4.98 | 4.98 |
| Sodium stearyl fumarate | 0.37 | 0.37 | 0.37 | 0.37 |
| Total weight | 100 | 100 | 100 | 100 |

Procedure:
a. Drug solution is prepared by dissolving minocycline, hydroxy propyl methyl cellulose, hydroxy propyl cellulose, polyethylene glycol and talc in water and layered onto inert core.
b. Barrier coating solution is prepared by dissolving hydroxy propyl methyl cellulose, followed by adding polyethylene glycol and talc with stirring.
c. Extended release coating solution is prepared by dissolving the required amount of ethyl cellulose and hydroxy propyl methyl cellulose in isopropyl alcohol, followed by adding triethyl cellulose.
d. Outer top or seal coating solution is prepared similarly as barrier coating solution.
e. Immediate release (IR) portion is prepared by coating barrier coating solution as prepared in step (b) onto drug loaded portion of step (a) and optionally followed by top or seal coating.
f. Extended release (ER) portion is prepared by coating extended release solution as prepared in step (c) onto drug loaded portion of step (a) followed by outer top or seal coating.
g. For examples 1, 3 & 4 accurately weighed amount of silicified microcrystalline cellulose, microcrystalline cellulose and sodium stearyl fumarate were blended with 20 percent of IR portions and 80 percent of ER portions and compressed into tablets with a single score.
h. For example 2, accurately weighed amount of silicified microcrystalline cellulose, microcrystalline cellulose and sodium stearyl fumarate were blended with 25 percent of IR portions and 75 percent of ER portions and compressed into tablets with a single score.
i. Compressed tablets of step (g) or (h) were packaged in a suitable pharmaceutical tablet storage bottle.

Example 5

The tablet comprising minocycline as prepared in example 4 was subjected to content uniformity studies as intact tablet and after dividing into two equal subunits. The results are shown in table 2.

TABLE 2

| Intact | Assay % - Example 4 | | |
|---|---|---|---|
| No. of units | Intact tablet | Division 1 | Division 2 |
| 1 | 101 | 99 | 95 |
| 2 | 99 | 102 | 95 |

TABLE 2-continued

| Intact | Assay % - Example 4 | | |
|---|---|---|---|
| No. of units | Intact tablet | Division 1 | Division 2 |
| 3 | 97 | 101 | 93 |
| 4 | 97 | 103 | 93 |
| 5 | 96 | 103 | 93 |
| 6 | 98 | 101 | 93 |
| 7 | 99 | 99 | 92 |
| 8 | 98 | 99 | 91 |
| 9 | 99 | 99 | 94 |
| 10 | 99 | 102 | 92 |
| Mean | 98.5 | 101 | 93 |
| Acceptance Value | 3.8 | 4 | 8.7 |
| % Relative standard deviation | 1.51 | 1.66 | 1.44 |
| Result | Pass | Pass | Pass |

Example 6

Figure 2:
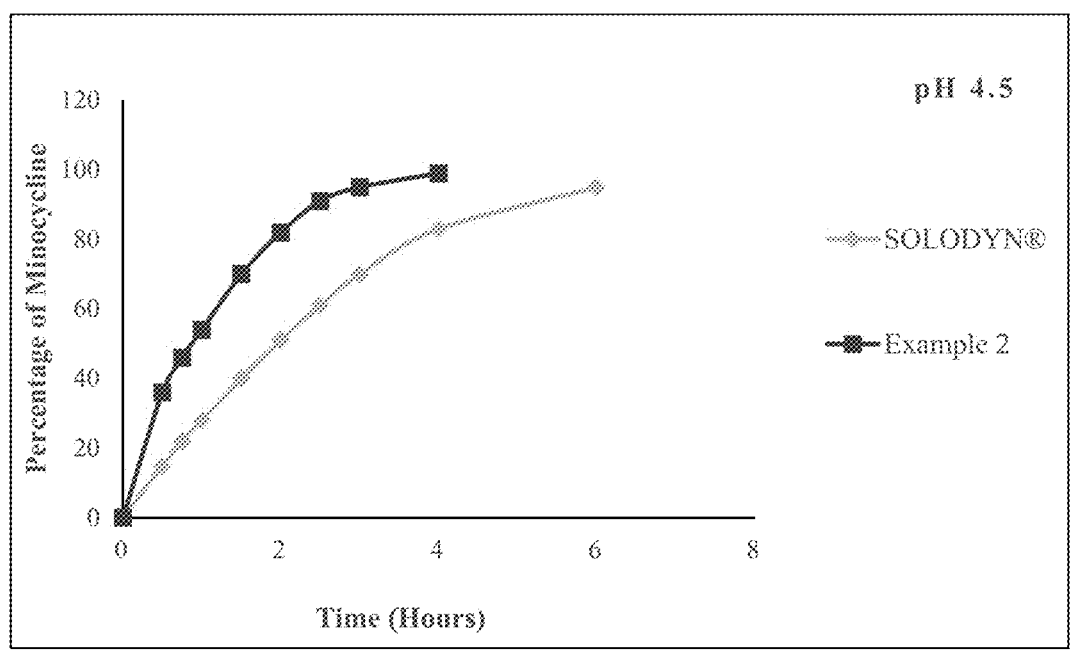
FIG. 2 shows in-vitro release profile for example 2 and SOLODYN® in 900 ml of pH 4.5, USP Type 1 apparatus at a speed of 100 rpm.
Figure 3:
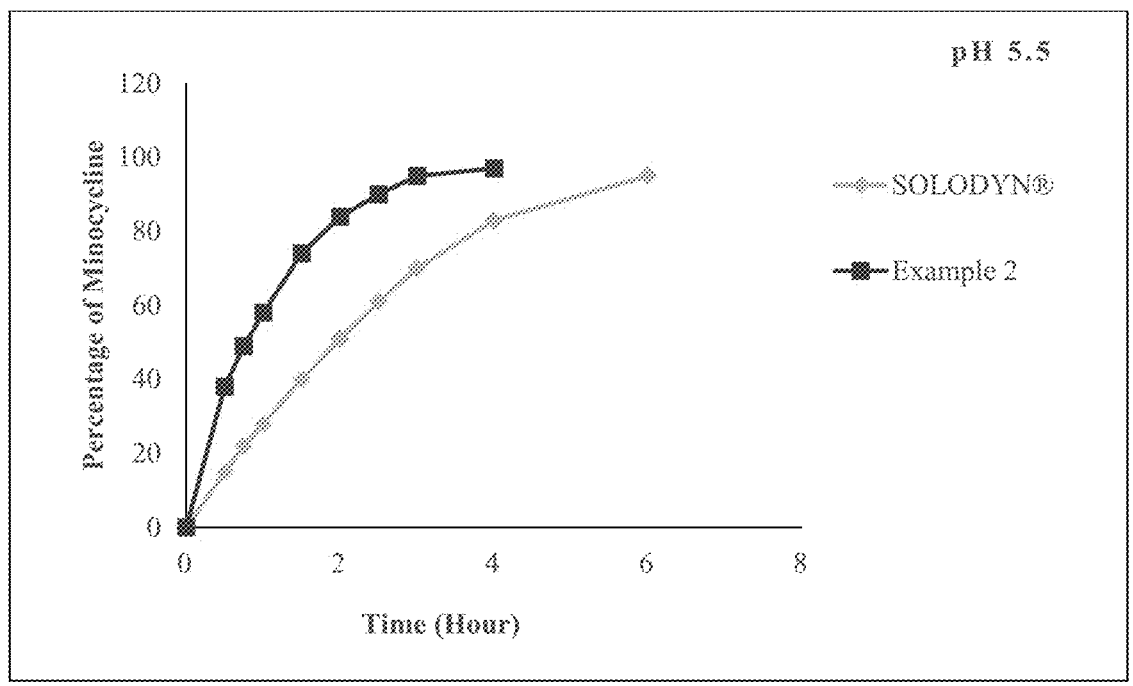
FIG. 3 shows in-vitro release profile for example 2 and SOLODYN® in 900 ml of pH 5.5, USP Type 1 apparatus at a speed of 100 rpm.

The tablet comprising minocycline as prepared in example 2 was subjected to dissolution studies in 900 ml of pH 2.1 Simulated Gastric Fluid, pH 4.5 acetate buffer and pH 5.5 phosphate buffer with USP Type I apparatus at a speed of 100 rpm and 37° C. till 6 hours and the in-vitro release profile are shown in FIGS. 1, 2 and 3 respectively.

Example 7

The tablet comprising minocycline as prepared in example 4 was subjected to disintegration studies in water and 1 table spoon of apple sauce, and results are given in table 3.

TABLE 3

| Disintegration time | | Assay (%) | |
|---|---|---|---|
| Water | Apple sauce | Initial | After 1 hr with apple sauce |
| 35-40 sec | 14-17 min | 101.3 | 99.6 |

Example 8

Figure 4A:
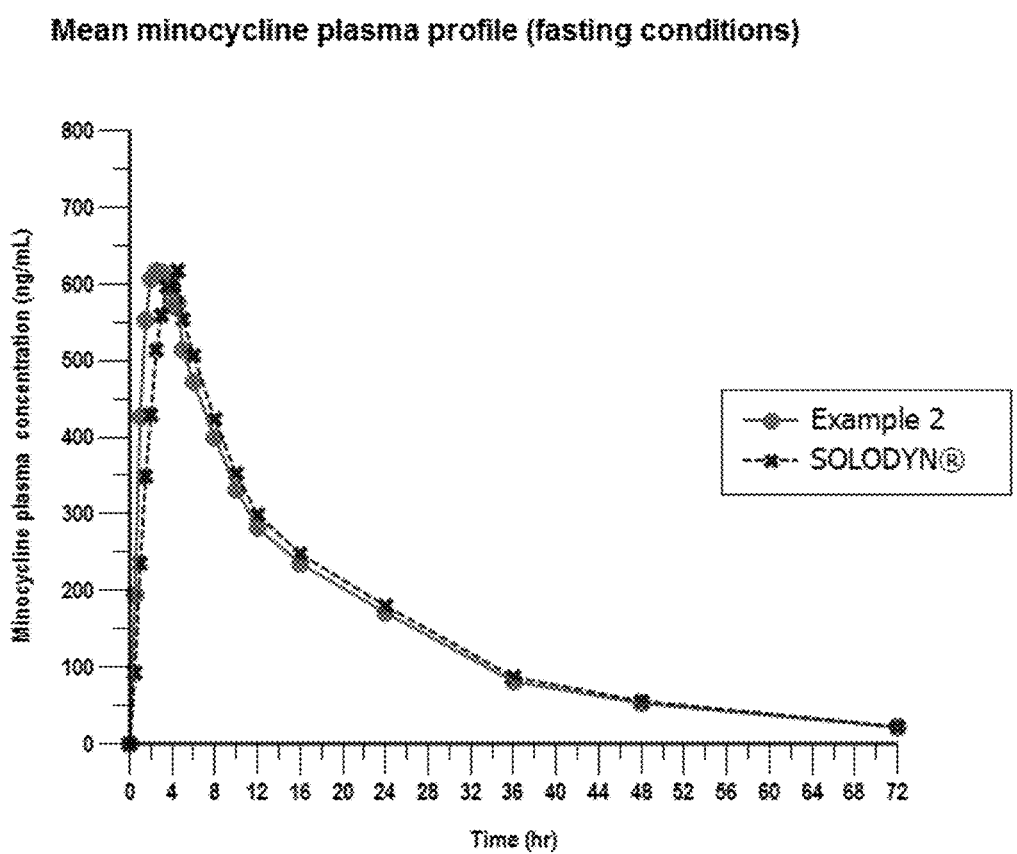
FIG. 4A shows 72 hour plasma minocycline concentration vs. time profile of example 2 equivalent to 135 mg of minocycline and SOLODYN® (80 mg+55 mg) administered to 77 healthy human subjects in fasting conditions.
Figure 4B:
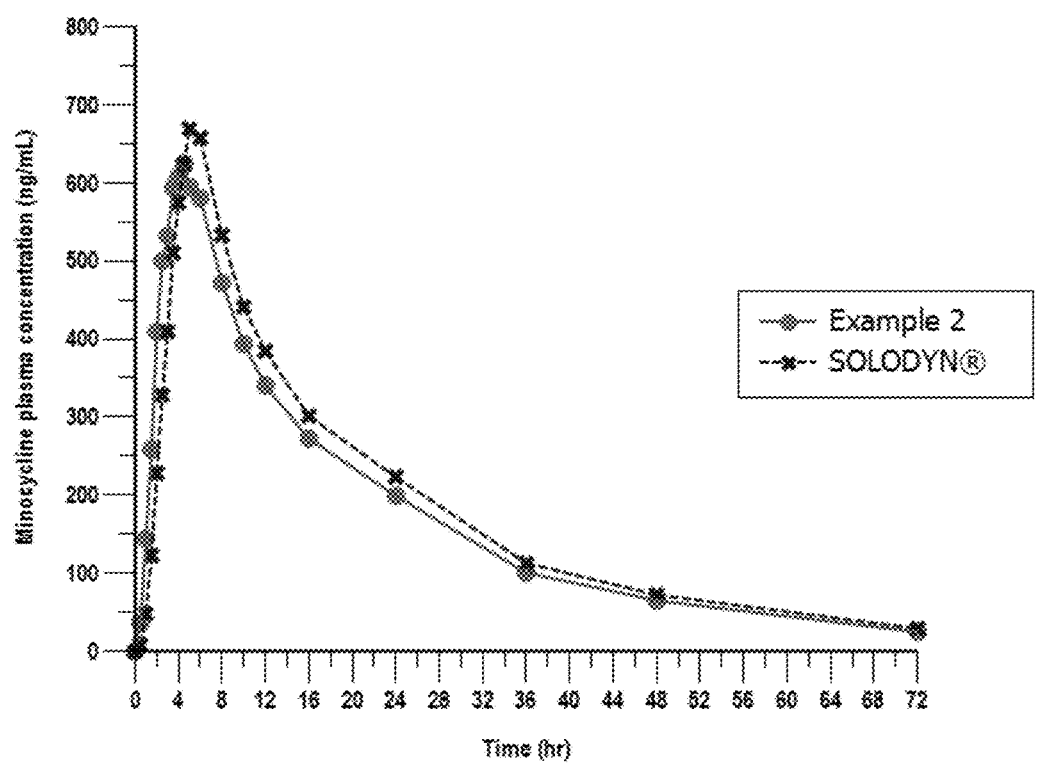
FIG. 4B shows 72 hour plasma minocycline concentration vs. time profile of example 2 equivalent to 135 mg of minocycline and SOLODYN® (80 mg+55 mg) administered to 77 healthy human subjects in fed conditions.

The pharmacokinetic parameters for minocycline tablets of the present application, was studied in comparison with SOLODYN® (80 mg+55 mg) oral tablets by using a two-way crossover method. The study was conducted in 77 healthy human subjects, in fasting and fed conditions and the subjects were administered a single dose of composition of Example 2 equivalent to 135 mg of minocycline. The results are shown in Table 4 and the mean plasma minocycline concentration vs. time profile for fasting and fed conditions vis-a-vis SOLODYN® is shown in FIGS. 4A and 4B.

TABLE 4

| Parameters | Example 2 | | SOLODYN® (80 mg + 55 mg) | |
|---|---|---|---|---|
| | Fasting conditions | Fed conditions | Fasting conditions | Fed conditions |
| $C_{max}$ (ng/mL) | 700 ± 261 | 707 ± 190 | 657 ± 230 | 750 ± 208 |
| $T_{max}$ (hr) | 2.01 | 3.50 | 4.00 | 5.00 |
| $t_{1/2}$ (hr) | 15.6 ± 2.46 | 17.1 ± 3.03 | 15.6 ± 2.62 | 17.6 ± 4.42 |
| $AUC_{(0-t)}$ (ng · hr/mL) | 10900 ± 3720 | 12000 ± 2970 | 11000 ± 3480 | 12900 ± 2820 |
| $AUC_{(0-\infty)}$ (ng · hr/mL) | 11400 ± 3890 | 12700 ± 3340 | 11600 ± 3690 | 13700 ± 3540 |

While several particular forms of the application have been illustrated and described, it will be apparent that various modifications and combinations of the application detailed in the text can be made without departing from the spirit and scope of the application.

What is claimed is:

1. A once daily oral compressed tablet comprising minocycline hydrochloride equivalent to 105 mg of minocycline consisting essentially of
   (i) immediate release pellets comprising (a) an inert core having a diameter of 125 to 600 microns, (b) a drug layer on the inert core, the drug layer comprising minocycline hydrochloride and (c) a barrier coating layer, the barrier coating comprising one or more polymers selected from methyl cellulose, carboxy methyl cellulose, hydroxy propyl cellulose, hydroxy propyl methyl cellulose, polyethylene glycol, starch, and any combination of any of the foregoing, wherein the only minocycline hydrochloride in the immediate release pellets is in the drug layer;
   (ii) extended release pellets comprising (a) an inert core having a diameter of 125 to 600 microns, (b) a drug layer on the inert core, the drug layer comprising minocycline hydrochloride and (c) a coating with one or more release modifying polymers to provide extended release of the minocycline hydrochloride in the drug layer of the extended release pellets, wherein the one or more release modifying polymers consist essentially of ethyl cellulose and hydroxy propyl methyl cellulose at a weight ratio of from 65:35 to 85:15 and in an amount of 5% to 10% by weight of the tablet, and the only minocycline hydrochloride in the extended release pellets is in the drug layer; and
   (iii) one or more cushioning agents to prevent adhesion of the pellets during compression, the one or more cushioning agents being selected from microcrystalline cellulose, silicified microcrystalline cellulose, calcium phosphate, mannitol, sorbitol, polyethylene glycol, sodium stearyl fumarate, magnesium stearate, starch, talc, or any combination of any of the foregoing;
   wherein the amount of cushioning agent(s) in the tablet ranges from 40% to 60% by weight, based upon 100% total weight of the tablet;
   minocycline hydrochloride is the sole active ingredient in the tablet;
   the immediate release pellets in total include minocycline hydrochloride equivalent to 21 to 42 mg of minocycline, and the extended release pellets in total include minocycline hydrochloride equivalent to 84 to 63 mg of minocycline; and
   the tablet having one score line for dividing the tablet into equal subunits to provide a predictable and accurate dose of minocycline and the divided subunits have (i) uniformity of drug content and (ii) similar dissolution profiles when measured in a USP type I apparatus at 100 rpm in 900 ml of simulated gastric fluid with a pH of 2.1 and at 37° C.

2. The tablet of claim 1, wherein in the immediate release pellets and the extended release pellets are present in a ratio of 20:80 to 40:60.

3. The tablet of claim 1, wherein the tablet is substantially free of (less than 5% w/w) lactose.

4. The tablet of claim 1, wherein the immediate release pellets are not coated with one or more release modifying polymers.

5. A once daily oral compressed tablet comprising minocycline hydrochloride equivalent to 135 mg of minocycline consisting essentially of
   (i) immediate release pellets comprising (a) an inert core having a diameter of 125 to 600 microns, (b) a drug layer on the inert core, the drug layer comprising minocycline hydrochloride and (c) a barrier coating layer, the barrier coating comprising one or more polymers selected from methyl cellulose, carboxy methyl cellulose, hydroxy propyl cellulose, hydroxy propyl methyl cellulose, polyethylene glycol, starch, and any combination of any of the foregoing, wherein the only minocycline hydrochloride in the immediate release pellets is in the drug layer;
   (ii) extended release pellets comprising (a) an inert core having a diameter of 125 to 600 microns, (b) a drug layer on the inert core, the drug layer comprising minocycline hydrochloride and (c) a coating with one or more release modifying polymers to provide extended release of the minocycline hydrochloride in the drug layer of the extended release pellets, wherein the one or more release modifying polymers consist essentially of ethyl cellulose and hydroxy propyl methyl cellulose at a weight ratio of from 65:35 to 85:15 and in an amount of 5% to 10% by weight of the tablet, and the only minocycline hydrochloride in the extended release pellets is in the drug layer; and
   (iii) one or more cushioning agents to prevent adhesion of the pellets during compression, the one or more cushioning agents being selected from microcrystalline cellulose, silicified microcrystalline cellulose, calcium phosphate, mannitol, sorbitol, polyethylene glycol, sodium stearyl fumarate, magnesium stearate, starch, talc, or any combination of any of the foregoing;
   wherein the amount of cushioning agent(s) in the tablet ranges from 40% to 60% by weight, based upon 100% total weight of the tablet;
   minocycline hydrochloride is the sole active ingredient in the tablet the immediate release pellets in total include minocycline hydrochloride equivalent to 27 to 54 mg of minocycline, and the extended release pellets in total include minocycline hydrochloride equivalent to 108 to 81 mg of minocycline; and the tablet having one score line for dividing the tablet into equal subunits to provide a predictable and accurate dose of minocycline and the divided subunits have (i) uniformity of drug content and (ii) similar dissolution profiles when measured in a USP type I apparatus at 100 rpm in 900 ml of simulated gastric fluid with a pH of 2.1 and at 37° C.

6. The tablet of claim 5, wherein the immediate release pellets are not coated with one or more release modifying polymers.

7. The tablet of claim 5, wherein in the immediate release pellets and the extended release pellets are present in a ratio of 20:80 to 40:60.

8. The tablet of claim 5, wherein the tablet is substantially free of (less than 5% w/w) lactose.

9. The tablet of claim 1, wherein said tablet is supplied to a pharmacy or stored in a warehouse to provide at least 50% reduced stock keeping units of minocycline tablets.

10. The tablet of claim 5, wherein said tablet is supplied to a pharmacy or stored in a warehouse to provide at least 50% reduced stock keeping units of minocycline tablets.

11. The tablet of claim 1, wherein the inert cores of the immediate release pellets and the inert cores of the extended release pellets comprise microcrystalline cellulose.

12. The tablet of claim 5, wherein the inert cores of the immediate release pellets and the inert cores of the extended release pellets comprise microcrystalline cellulose.

13. The tablet of claim 1, wherein the coating on the extended release pellets consists essentially of ethyl cellulose, hydroxy propyl methyl cellulose, and a plasticizer.

14. The tablet of claim 13, wherein the plasticizer is triethyl citrate.

15. The tablet of claim 5, wherein the coating on the extended release pellets consists essentially of ethyl cellulose, hydroxy propyl methyl cellulose, and a plasticizer.

16. The tablet of claim 15, wherein the plasticizer is triethyl citrate.

17. The tablet of claim 1, wherein said tablet exhibits a disintegration time from 5 minutes to 20 minutes in a food dispersion.

18. The tablet of claim 5, wherein said tablet exhibits a disintegration time from 5 minutes to 20 minutes in a food dispersion.

* * * * *